US008048635B2

(12) United States Patent
Burkly et al.

(10) Patent No.: US 8,048,635 B2
(45) Date of Patent: Nov. 1, 2011

(54) MEASUREMENT OF SOLUBLE TWEAK LEVELS FOR EVALUATION OF LUPUS PATIENTS

(75) Inventors: Linda C. Burkly, West Newton, MA (US); Jennifer Michaelson, Brighton, MA (US); Chaim Putterman, Bergenfield, NJ (US)

(73) Assignees: Biogen Idec MA Inc., Cambridge, MA (US); Albert Einstein College of Medicine of Yeshiva University, Bronx, NY (US)

( * ) Notice: Subject to any disclaimer, the term of this patent is extended or adjusted under 35 U.S.C. 154(b) by 449 days.

(21) Appl. No.: 11/953,360

(22) Filed: Dec. 10, 2007

(65) Prior Publication Data
US 2008/0292622 A1 Nov. 27, 2008

Related U.S. Application Data

(63) Continuation of application No. PCT/US2006/022830, filed on Jun. 12, 2006.

(60) Provisional application No. 60/689,905, filed on Jun. 13, 2005.

(51) Int. Cl.
G01N 33/53 (2006.01)
G01N 33/566 (2006.01)
C07K 16/28 (2006.01)

(52) U.S. Cl. ............. 435/7.1; 436/501; 530/388.24

(58) Field of Classification Search .............. None
See application file for complete search history.

(56) References Cited

U.S. PATENT DOCUMENTS

| | | |
|---|---|---|
| 6,207,642 B1 | 3/2001 | Wiley |
| 6,727,225 B2 | 4/2004 | Wiley |
| 6,824,773 B2 | 11/2004 | Wiley |
| 6,943,146 B2 | 9/2005 | Jakubowski et al. |
| 7,087,725 B2 | 8/2006 | Browning et al. |
| 7,109,298 B2 | 9/2006 | Browning et al. |
| 7,129,061 B1 | 10/2006 | Browning et al. |
| 7,169,387 B2 | 1/2007 | Rennert |
| 7,208,151 B2 | 4/2007 | Browning et al. |
| 7,482,430 B2 | 1/2009 | Wiley |
| 7,495,086 B2 | 2/2009 | Kim et al. |
| 7,507,807 B2 | 3/2009 | Wiley |
| 7,517,962 B2 | 4/2009 | Wiley |
| 7,566,769 B2 | 7/2009 | Browning et al. |
| 2002/0015703 A1 | 2/2002 | Rennert |
| 2004/0176296 A1 | 9/2004 | Holtzman et al. |
| 2004/0203083 A1* | 10/2004 | Buechler et al. ........... 435/7.92 |
| 2006/0003932 A1 | 1/2006 | Jakubowski et al. |
| 2006/0240004 A1 | 10/2006 | Burkly et al. |
| 2006/0252122 A1 | 11/2006 | Browning et al. |
| 2007/0110745 A1 | 5/2007 | Rennert |
| 2007/0280940 A1 | 12/2007 | Winkles et al. |
| 2008/0008714 A1 | 1/2008 | Browning et al. |
| 2008/0187544 A1 | 8/2008 | Burkly et al. |
| 2008/0241163 A1 | 10/2008 | Burkly et al. |
| 2008/0279853 A1 | 11/2008 | Burkly et al. |
| 2008/0286271 A1 | 11/2008 | Ashkenazi et al. |
| 2008/0292622 A1 | 11/2008 | Burkly et al. |
| 2009/0068102 A1 | 3/2009 | Burkly et al. |
| 2009/0124993 A1 | 5/2009 | Burkly et al. |

FOREIGN PATENT DOCUMENTS

| | | |
|---|---|---|
| EP | 1354950 | 10/2003 |
| EP | 1566636 A1 | 8/2005 |
| WO | WO 98/05783 A1 | 2/1998 |
| WO | WO 98/35061 A2 | 8/1998 |
| WO | WO 99/19490 A1 | 4/1999 |
| WO | WO 00/42073 A1 | 7/2000 |
| WO | WO 01/45730 A2 | 6/2001 |
| WO | WO 01/85193 A2 | 11/2001 |
| WO | WO 02/22166 A2 | 3/2002 |
| WO | WO 02/102994 | 12/2002 |
| WO | WO 03/040307 | 5/2003 |
| WO | WO 03/086311 A2 | 10/2003 |
| WO | WO 2005/080972 A1 | 9/2005 |
| WO | WO 2006/047172 A1 | 5/2006 |
| WO | WO 2006/052926 A2 | 5/2006 |
| WO | WO 2006/088890 A2 | 8/2006 |
| WO | WO 2006/089095 A2 | 8/2006 |
| WO | WO 2006/096487 A2 | 9/2006 |
| WO | WO 2006/122187 A2 | 11/2006 |
| WO | WO 2006/130374 A2 | 12/2006 |
| WO | WO 2006/130429 A2 | 12/2006 |
| WO | WO 2006/138219 A2 | 12/2006 |
| WO | WO 2008/048924 A2 | 4/2008 |

OTHER PUBLICATIONS

Kawakita T, et al. Functional expression of TWEAK in human hepatocellular carcinoma: possible implication in cell proliferation and tumor angiogenesis. Biochemical and Biophysical Research Communications, 2004, vol. 318, p. 723-733.*
Wada T, et al. Detection of urinary interleukin-8 in glomerular diseases. Kidney International, 1994, vol. 46, p. 455-460.*
Saemann M, et al. Urinary tract infection in renal transplant recipients. Eur. J. Clin. Invest., 2008, vol. 38(S2), p. 58-65.*
Chicheportiche, Y. et al. TWEAK, a new secreted ligand in the tumor necrosis factor family that weakly induces apoptosis. Journal of Biological Chemistry, 1991, vol. 272, No. 51, p. 32401-32410.*
Campbell et al., "The Role of Tweak/Fn14 in the Pathogenesis of Inflammation and Systemic Autoimmunity", Frontiers in Bioscience, vol. 9:2273-2284 (2004).
Putterman et al., "Tweak Blockade Improves Kidney Disease in Lupus-Prone Mice: A Novel Approach to the Treatment of Lupus Nephritis?", Abstract #562.27, Fed. of Amer. Soc. For Experimental Biol., vol. 18, No. 5 (2004).
International Search Report dated Jan. 26, 2007 for international application No. PCT/US2006/022830.
Boucraut, J. et al., "Anti-TWEAK Monoclonal Antibodies Reduce CNS Immune Cell Infiltration and Severity of Experimental Autoimmune Encephalomyelitis" Meeting: Autoimmunity: Mechanisms and Novel Treatments, Mykonos, Greece, Oct. 8-13, 2003; Aegean Conference Series, vol. 12, Abstract 64, p. 89 (2003).

(Continued)

Primary Examiner — Robert Landsman
Assistant Examiner — Bruce D Hissong
(74) Attorney, Agent, or Firm — Finnegan, Henderson, Farabow, Garrett & Dunner, L.L.P.

(57) ABSTRACT

Methods of treating patients and evaluating patients for disease stage and/or severity are disclosed.

18 Claims, 5 Drawing Sheets

OTHER PUBLICATIONS

Campbell, S. et al., "Proinflammatory Effects of TWEAK/Fn14 Interactions in Glomerular Mesangial Cells", J. Immunol. 176:1889-1898 (2006).

Chicheportiche, Y. et al., "Proinflammatory Activity of TWEAK on Human Dermal Fibroblasts and Synoviocytes: Blocking and Enhancing Effects of Anti-TWEAK Monoclonal Antibodies", Arthritis Res. 4(2):126-33 (2002). Epub Nov. 9, 2001.

Desplat-Jego, S. et al., "Anti-TWEAK monoclonal antibodies reduce immune cell infiltration in the central nervous system and severity of experimental autoimmune encephalomyelitis", Clin. Immunol. 117(1):15-23 (2005).

Desplat-Jego, S. et al., "TWEAK Is Expressed by Glial Cells, Induces Astrocyte Proliferation and Increases EAE Severity", J. Neuroimmunol. 133:116-123 (2002).

Kalled et al., "Anti-CD40 Ligand Antibody Treatment of SNF.sub.1 Mice with Established Nephritis: Preservation of Kidney Function", J. Immunol. 160:2158-2165 (1998).

Kaplan et al., "The Apoptotic Ligands TRAIL, TWEAK, and Fas Ligand Mediate Monocyte Death Induced by Autologous Lupus T Cells", J. Immunol. 169:6020-6029 (2002).

Mueller, A.M. et al., "Targeting fibroblast growth-factor-inducible-14 signaling protects from chronic relapsing experimental autoimmune encephalomyelitis", J. Neuroimmunol. 159(1-2):55-65 (2005).

Perper, S.J. et al., "TWEAK is a novel arthritogenic mediator", J. Immunol. 177(4):2610-2620 (Aug. 15, 2006).

Potrovita, I. et al., "TWEAK—A Regulator of Neuronal Cell Death", Naunyn-Schmiedeberg's Archives of Pharmacology 369(Suppl. 1):R12 (Mar. 9, 2004).

Rovin et al., "Urine chemokines as biomarkers of human systemic lupus erythematosus activity", J. Am. Soc. Nephrol. 16:467-473 (2005).

Saas, P. et al., "TWEAK Stimulation of Astrocytes and the Proinflammatory Consequences", GLIA 32(1):102-107 (2000).

U.S. Appl. No. 11/422,191 by Browning, et al., filed Jun. 5, 2006.

Zhao, Z. et al., "TWEAK/Fn14 Interactions Are Instrumental in the Pathogenesis of Nephritis in the Chronic Graft-versus-Host Model of Systemic Lupus Erythematosis", J. Immunol. 179:7949-7958 (2007).

* cited by examiner

US 8,048,635 B2

MEASUREMENT OF SOLUBLE TWEAK LEVELS FOR EVALUATION OF LUPUS PATIENTS

CROSS-REFERENCE TO RELATED APPLICATIONS

This application, filed under 35 U.S.C. §111, is a continuation claiming priority under 35 U.S.C. §120 of International Application No. PCT/US2006/022830, filed on Jun. 12, 2006, which claims priority to U.S. Application Ser. No. 60/689,905, filed on Jun. 13, 2005. The contents of all the foregoing applications are hereby incorporated by reference.

BACKGROUND

The identification of genes and proteins linked with the severity and/or progression of disease and the development of diagnostic methods to identify and/or monitor disease progression are of considerable importance.

SUMMARY OF THE INVENTION

The invention is based, at least in part, on the discovery that Tweak and/or Tweak receptor, e.g., Fn14 (and certain proteins that are modulated, e.g., induced, by Tweak) can be used as biomarkers of disease activity in a biological fluid of a human subject. Accordingly, methods and compositions are provided for assessing, staging, and/or monitoring disease activity in a subject, e.g., assessing, staging, and/or monitoring inflammatory disease activity (e.g., lupus, fibrosis, rheumatoid arthritis, multiple sclerosis, and nephritis activity, e.g., lupus nephritis); and neurodegenerative disease activity.

Accordingly, in one aspect, the invention features a method of evaluating a subject. The method includes evaluating Tweak or Fn14 (and/or certain proteins that are increased by Tweak), in a biological fluid of a subject (such as a human), and correlating the result of the evaluation with the subject's risk, stage or status of disease activity, e.g., inflammatory disease activity. The subject can have, or be at risk for, e.g., an inflammatory condition such as lupus, rheumatoid arthritis (RA), psoriatic arthritis (PsA), multiple sclerosis, nephritis (e.g., interstitial nephritis, lupus nephritis, glomerulonephritis (GN), mesangial GN, membraneous GN, diffuse proliferative GN and/or membranoproliferative GN), stroke or a neurodegenerative disease (e.g., ALS, Parkinson's Disease, Huntington's Disease, Alzheimer's Disease), fibrosis, or cancer (e.g., solid cancers and/or hematological cancers). The term "correlating" means describing the relationship between the presence or level of the protein or nucleic acid, and the stage, status, extent, severity, or level of risk for disease. Such correlation may be displayed in a record, e.g., a print or computer readable material, e.g., an informational, diagnostic, or instructional material. The record may identify the presence or level of a Tweak or Tweak-R protein or nucleic acid as a diagnostic, staging or prognostic factor for the disease. The record may include a parameter (qualitative or quantitative) representing expression or activity of Tweak and/or TweakR, as evaluated by the method.

The evaluation is performed on a biological fluid from the subject, e.g., serum, urine, plasma, cerebrospinal fluid (CSF), or synovial fluid. Increased Tweak or TweakR protein levels in the fluid correlate (e.g., directly) with increased severity, stage and/or activity of disease. The ability to perform such an evaluation on a readily obtainable biological fluid from a subject provides a simple, quick, relatively non-invasive method for evaluating, staging, and/or diagnosing a subject, e.g., before, during and/or after a treatment is begun.

In one embodiment, increased Tweak or TweakR urinary, serum or plasma levels correlate with increased severity or activity of renal disease (e.g., more advanced stage or increased severity of nephritis, e.g., lupus nephritis) compared to a reference value. In another embodiment, increased Tweak or TweakR serum, plasma, urine or synovial fluid levels correlate with increased severity or activity of RA compared to a reference value. In another embodiment, increased Tweak or TweakR serum, plasma, or urine fluid levels correlate with increased severity or activity of lupus compared to a reference value. In another embodiment, increased Tweak or TweakR serum, plasma, urine or CSF levels correlate with increased severity or activity of MS or a neurodegenerative disease compared to a reference value. In another embodiment, increased Tweak or TweakR serum, plasma, or urine levels correlate with increased severity or activity of fibrosis compared to a reference value. A reference value can be a control value, e.g., a value for a normal subject (e.g., a subject not suspected of, or at risk for, the disease being evaluated), a value determined for a cohort of subjects, or a baseline (e.g., prior) value from the subject being evaluated.

The method can be used to stage and/or diagnose a disorder, e.g., to diagnose the stage or severity of the disorder; to evaluate the subject's response to treatment, e.g., to monitor progression or improvement in a parameter of the disorder in a subject being treated for the disorder; to evaluate the course of the disorder, e.g., to assess the risk of, or to predict a flare-up of, the disorder. In one embodiment, the evaluation is performed more than once, e.g., at periodic intervals over a period of time, e.g., to monitor progression of the disease or to monitor response to a treatment. For example, the evaluation may be performed daily, every 2 or 3 days, every week, every 2 weeks, monthly, every 6 weeks, every 2 months, every 3 months or as appropriate, over a period of time to encompass at least 2, 3, 5, 10 evaluations or more.

In some embodiments, the step of evaluating includes detecting expression or activity of a Tweak or Tweak-R protein or a nucleic acid encoding Tweak or Tweak-R (e.g., by qualitative or quantitative analysis of mRNA, cDNA, or protein), or evaluating one or more nucleotides in a nucleic acid (genomic, mRNA, or cDNA) encoding Tweak or Tweak-R. In one embodiment, the method includes using an immunoassay to detect Tweak protein, e.g., in a biological fluid, such as a urine sample, of the subject. In other embodiments, the method can include administering a labeled Tweak or Tweak-R binding agent (e.g., an antibody) to a subject, and evaluating localization of the labeled binding agent in the subject, e.g., by imaging the subject (e.g., imaging at least a portion of the kidney of the subject).

In one embodiment, the subject has nephritis, or is suspected of having nephritis. The method can be used to evaluate a treatment for renal disease, e.g., nephritis, e.g., lupus nephritis. For example, the subject is receiving a treatment for renal disease and the subject is evaluated before, during, or after receiving the treatment, e.g., multiple times during the course of treatment. The subject may have normal kidney function as defined and detected by a clinical measure, e.g., urine protein level, blood creatinine level, urine creatinine level, creatinine clearance, and/or blood urea nitrogen. In other cases, the subject has an abnormal, e.g., deficient, kidney function, e.g., as defined and detected by a clinical measure.

In one embodiment, the subject has arthritis, e.g., rheumatoid arthritis (RA) or psoriatic arthritis (PsA), or is suspected of having arthritis. The method can be used to evaluate a treatment for arthritis. For example, the subject is receiving a treatment for arthritis (e.g., an anti-TNF therapy, methotrexate or steroids) and the subject is evaluated before, during, or after receiving the treatment, e.g., multiple times during the course of treatment.

In one embodiment, the subject has lupus. The subject may have, e.g., lupus nephritis, and/or neuropsychiatric manifestations (CNS lupus) or other manifestations of lupus, e.g., low blood count, serositis or hematological manifestations. The method can be used to evaluate a treatment for lupus. For example, the subject is receiving a treatment for lupus (e.g., NSAID, corticosteroids, or a DMARD) and the subject is evaluated before, during, or after receiving the treatment, e.g., multiple times during the course of treatment.

In one embodiment, the subject has a neurodegenerative disease, e.g., MS, Parkinson's Disease, Huntington's Disease, Alzheimer's Disease or ALS, or is suspected of having a neurodegenerative disease. The method can be used to evaluate a treatment for a neurodegenerative disease. For example, the subject is receiving a treatment for a neurodegenerative disease (e.g., beta-interferon, riluzole, a cholinesterase inhibitor, copaxone, an NMDA receptor antagonist) and the subject is evaluated before, during, or after receiving the treatment, e.g., multiple times during the course of treatment.

The method can be used to identify a subject for treatment, e.g., for treatment for nephritis, lupus, fibrosis, rheumatoid arthritis, psoriatic arthritis, stroke, cancer or a neurodegenerative disease. The subject can be identified as a subject suited for treatment as a function of results of the detection, e.g., the results show similarity to, e.g., statistically significant similarity to, a reference value indicative of a subject being at a particular stage of the particular disease. For example, elevated Tweak or Tweak-R expression in the urine, serum, plasma, or CSF can be indicative of a subject who can be treated with a Tweak or Tweak-R blocking agent or other treatment for the disease.

An increase identified by the evaluation step, e.g., a statistically significant increase, or at least 20%, 25%, 30, 50, 70, 80, 100, or 110% increase, in a subject, over a reference value, e.g., a base value or control, can indicate increased activity or severity of the disease, e.g., lupus nephritis (e.g., membranous, focal proliferative, or diffuse proliferative lupus nephritis). For example, a 10%, 20%, 25% or greater increase in urine Tweak levels (e.g., relative to creatinine) compared to a negative control, baseline value, or previous evaluation in a subject indicates increased nephritis severity or activity. In one embodiment, Tweak levels greater than 0.5, 1, 2, 3, 4, or 5 pg/mg Cr can indicate that the subject has nephritis, e.g., lupus nephritis. In one embodiment, Tweak levels in the range of 2-8 pg/mg Cr (e.g., about 2, 2.5, 3, 3.5, 4, 4.5, 5, 5.5, 6, 6.5, 7, or 7.5 pg/mg Cr) can indicate that the subject has stable disease; Tweak levels in the range of 8-10 pg/mg Cr can indicate that the subject is at risk for a relapse; Tweak levels greater than 10 pg/mg Cr (e.g., between 10-15 pg/mg Cr) can indicate that the subject is in active relapse.

In one embodiment, the method includes evaluating the subject (e.g., evaluating urine samples from the subject) a plurality of instances over time, e.g., over the course of a treatment, e.g., at least one day, five days, a week, four or six weeks, and so forth. The method can include determining a rate of change for the evaluated parameter, e.g., to determine disease progression or therapeutic efficacy. In one embodiment, the subject is also being treated, e.g., with a Tweak blocking agent or other treatment for the disease.

In one embodiment, the evaluation includes contacting a biological sample of the subject, preferably a urine, serum, plasma, CSF or synovial fluid sample, with an agent that detects Tweak, TweakR or a biomarker whose expression is modulated (e.g., increased) by Tweak (e.g., in mesangial cells). The agent, e.g., an antibody or nucleic acid probe, can be immobilized on a solid phase, e.g., on a microtiter well, tube, dipstick or other test device. In a preferred embodiment, the expression, presence, level, or activity is detected using a dipstick or other test device format assay.

The evaluation can include a protein-based (e.g., an immunoassay) or nucleic acid-based assay, e.g., a hybridization-based assay. In one embodiment, the evaluating step comprises performing one or more of: enzyme-linked immunoassay, radioimmunoassay, immunoblot assay (including Western blot analysis and sandwich assay), in situ hybridization, Northern blot analysis, and nucleic acid amplification, including PCR (e.g. quantitative RT-PCR). Many evaluation methods can include one or more features of the foregoing. Exemplary immunoassays can include contacting the sample with an antibody that binds to Tweak or can be adapted to use other agents that bind to Tweak, e.g., a soluble Tweak receptor. Nucleic acid-based assays can include hybridization with a nucleic acid from a Tweak-encoding sequence, e.g., from a human Tweak-encoding genomic sequence or cDNA, e.g., the coding or non-coding strand, or a primer or other oligonucleotide complementary to a region of a Tweak-encoding sequence. It is also possible to evaluate a biomarker that is modulated (e.g., increased) by Tweak.

In some embodiments, evaluation can be facilitated by a dipstick or other test device-based kit, e.g., suitable for testing by non-trained individuals, e.g., suitable for home testing. Such a screening test would provide convenience, privacy and eliminate the necessity and cost of visiting a physician for a screening test, although the dipstick or other test device kit could also be used in a clinical setting. The dipstick or other test device kit could be similar to a home pregnancy kit, known to those of skill in the art, and could provide a color indication for an increased risk, stage or severity for an inflammatory condition, e.g., nephritis, based upon the levels of a protein described herein, e.g., Tweak, TweakR or a biomarker whose expression modulated (e.g., increased) by Tweak, in the sample. Such a dipstick or other test device-based kit could be provided with a small plastic cup for collecting and retaining the sample and for conducting the test. In one scenario, the dipstick or other test device can react to produce one color if a reference level of a first protein, e.g., Tweak, is exceeded, a different color if a reference level of a second protein, e.g., a biomarker whose expression modulated (e.g., increased) by Tweak, is exceeded, and when both levels are exceeded, the two colors will combine to yield a third color that is easily distinguishable from the others. For example, a dipstick or other test device that turns yellow when a reference level of Tweak is exceeded, and turns blue when a reference level of the biomarker is exceeded will turn green when both levels are exceeded. Because a dipstick or other test device-based assay kit would be relatively resistant to temperature and humidity variations, it could easily be transported, stored and used virtually anywhere. In one embodiment, the kit includes at least 1, e.g., at least 2, 5, 10, 20, 30, or 50, test devices, e.g., dipsticks, e.g., membranes, e.g., membrane strips described herein. In one embodiment, the kit contains a container suitable for collecting a urine sample. The kit can also contain a device to obtain a tissue sample, such as a cotton swab or wooden swab.

In another embodiment, the method of the present invention may be utilized in combination with a densitometer in a device for use in a setting such as a doctor's office, a clinic or a hospital. The densitometer can provide rapid measurement of the optical density of dipstick or other test device strips that have been contacted with a bodily fluid or tissue.

In one embodiment, the method additionally includes treating the subject for the condition being evaluated, e.g., nephritis. For example, the method includes: identifying a subject at risk for or having lupus nephritis. The method can further include providing the subject a treatment for lupus, e.g., a Tweak blocking agent or other treatment suitable for treating lupus nephritis, e.g., corticosteroids or other immunosuppressive medications.

In a preferred embodiment, the subject is further evaluated for one or more of the following parameters: albumin levels; glucose levels; urine creatine; urine protein, and so forth.

In a preferred embodiment, the evaluation is used to choose a course of treatment. For example, if the subject is determined to be at risk for loss of renal function or renal disease, the treatment can include dietary restrictions.

In one embodiment, the evaluation is performed by the subject. In another embodiment, the evaluation is performed by a health care provider. In yet another embodiment, the evaluation is performed by a third party.

The method can also be used to select a patient population for treatment. A set of one or more subjects indicated for renal inflammation, e.g., relative to a reference are selected. The subjects of the set are administered a Tweak blocking agent or other treatment for renal inflammation, e.g., for renal nephritis.

Subjects can also be evaluated in response to other indications, e.g., signs of early disease, e.g., loss of renal function, when a renal disorder, e.g., early loss of renal function, is diagnosed; before, during or after a treatment for an a renal disorder, is begun or begins to exert its effects; or generally, as is needed to maintain health, e.g., kidney health, e.g., throughout the natural aging process. The period over which the agent is administered (or the period over which clinically effective levels are maintained in the subject) can be long term, e.g., for six months or more or a year or more, or short term, e.g., for less than a year, six months, one month, two weeks or less.

The method can also include obtaining a profile, e.g., the profile including parameters (qualitative or quantitative) representing expression or activity of a plurality of biomarkers, e.g., one or more of (preferably at least two of): Tweak and a biomarker whose expression modulated (e.g., increased) by Tweak (e.g., RANTES, KC, and/or IP-10). The profile can be compared to a reference profile, e.g., using multi-dimensional analysis, e.g., distance functions. A computer medium can be used that has executable code for effecting one or more the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of expression of Tweak RANTES, KC, and/or IP-10. The record can further include a subject identifier, e.g., a patient identifier, and optionally other clinical information, e.g., information that assesses a inflammatory response or autoimmune response.

Targeting of the Tweak pathway (e.g., with a Tweak pathway inhibitor such as an agent that blocks a Tweak-TweakR interaction, e.g., an anti-Tweak or anti-Fn14 blocking antibody) can be used in the treatment of nephritis, e.g., lupus nephritis.

In another aspect, the disclosure features a method of treating nephritis. The method includes: administering, to a subject (e.g., a human subject) who has or is at risk for nephritis, a Tweak blocking agent, e.g., in an amount and for a time to provide a therapeutic effect. In one embodiment, the agent is an antibody, e.g., a Tweak or Fn14 antibody, or a soluble form of Tweak receptor, e.g., a soluble Fn14.

In one embodiment, the subject has lupus. In such embodiments, the Tweak blocking agent is effective to treat the renal manifestations of the lupus, e.g., to treat lupus nephritis.

In one embodiment, the disorder is acute nephritis, chronic nephritis, glomerulonephritis (GN), primary glomerulonephritis, autoimmune nephritis, pyelonephritis, mesangial GN, membraneous GN, diffuse proliferative GN membranoproliferative GN and/or interstitial nephritis. In one embodiment the nephritis is not rapidly progressive crescentic glomerulonephritis.

In one embodiment, the agent is an antibody that is a full length IgG. In other embodiments, the agent is an antigen-binding fragment of a full length IgG, e.g., the agent is a single chain antibody, Fab fragment, F(ab')2 fragment, Fd fragment, Fv fragment, or dAb fragment. In preferred embodiments, the antibody is a human, humanized or humaneered antibody or antigen-binding fragment thereof.

In one embodiment, the agent is a soluble form of the Tweak receptor, e.g., a polypeptide at least 95% identical to amino acids 28-X1 of SEQ ID NO:2, where amino acid X1 is selected from the group of residues 68 to 80 of SEQ ID NO:2. In some cases, the soluble form of the receptor is fused with a heterologous polypeptide, e.g., an antibody Fc region.

In one embodiment, the agent is administered in an amount sufficient to reduce urinary protein levels, delay or prevent additional kidney function deterioration, and/or improve kidney function.

In one embodiment, the agent is administered at a dose between 0.1-100 mg/kg, between 0.1-10 mg/kg, between 1 mg/kg-100 mg/kg, between 0.5-20 mg/kg, or 1-10 mg/kg. In the most typical embodiment, the dose is administered more than once, e.g., at periodic intervals over a period of time (a course of treatment). For example, the dose may be administered every 2 months, every 6 weeks, monthly, biweekly, weekly, or daily, as appropriate, over a period of time to encompass at least 2 doses, 3 doses, 5 doses, 10 doses, or more.

In one embodiment, the agent is administered in combination with another therapy for lupus or nephritis, e.g., corticosteroids or NSAIDs.

In some cases, the subject can be identified by performing a diagnostic assay described herein, e.g., by evaluating a urine sample from the subject, e.g., by evaluating Tweak levels or expression of a biomarker whose expression is increased by Tweak in mesangial cells. Exemplary biomarkers include RANTES, KC, and/or IP-10. Tweak or the biomarker can be detected by a variety of methods, including an immunoassay.

The term "treating" refers to administering a therapy in an amount, manner, and/or mode effective to improve or prevent a condition, symptom, or parameter associated with a disorder or to prevent onset, progression, or exacerbation of the disorder (including secondary damage caused by the disorder), to either a statistically significant degree or to a degree detectable to one skilled in the art. Accordingly, treating can achieve therapeutic and/or prophylactic benefits. An effective amount, manner, or mode can vary depending on the subject and may be tailored to the subject.

In another aspect, the invention features a method of evaluating a compound, e.g., screening for a compound, that modulates renal function. The method includes contacting a test compound to a Tweak or TweakR protein, a cell, a tissue or a test subject, e.g., a non-human mammal, and evaluating the protein, cell, tissue or test subject for Tweak or TweakR expression or function. A test compound that decreases or inhibits Tweak or TweakR expression or function is identified as a compound that modulates renal function, e.g., a compound useful to treat nephritis. In one embodiment, the test compound interacts with Tweak or TweakR, directly or indirectly. In a preferred embodiment, the test compound is a small molecule; a protein or peptide; an antibody; and/or a nucleotide sequence. For example, the agent can be an agent identified through a library screen.

In some embodiments, the method may include a two-step assay, e.g., a first step of contacting and evaluating a test compound against a Tweak or TweakR protein or a Tweak expressing cell, and a second step of contacting and evaluating the test compound against a non-human animal.

The method can also include evaluating expression or activity (in the cell, tissue or non-human animal) of one or more biomarkers whose expression modulated (e.g., increased) by Tweak (e.g., RANTES, KC, and/or IP-10).

In another aspect, the disclosure features a method of making a diagnostic device. The method includes supplying a substrate, e.g., a dipstick or other test device, well, tube, or strip; and adhering an reagent (e.g., an antibody) that detects one or more of Tweak, TweakR or a biomarker increased by Tweak, or providing such reagent as a solution or other formulation available for use in the test device, e.g., in a sandwich assay. In one embodiment, the reagent is applied by spraying, deposition of a liquid, or printing. The device can be supplied with instruction for its use in the evaluation of kidney disease, e.g., nephritis.

In another aspect, the invention features a computer readable record encoded with (a) a subject identifier, e.g., a patient identifier, (b) one or more results from an evaluation of the subject, e.g., a diagnostic evaluation described herein, e.g., the level of expression, level or activity of Tweak or Tweak-R, in the subject, and optionally (c) a value for or related to renal disease (such as nephritis), e.g., a value correlated with disease status or risk with regard to renal disease. In one embodiment, the invention features a computer medium having a plurality of digitally encoded data records. Each data record includes a value representing the expression, level or activity of Tweak or Tweak-R levels or activity, in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression, level or activity of genes other than Tweak or Tweak-R (e.g., other genes associated with renal disease, or other genes on an array). The data record can be structured as a table, e.g., a table that is part of a database such as a relational database (e.g., a SQL database of the Oracle or Sybase database environments). The invention also includes a method of communicating information about a subject, e.g., by transmitting information, e.g., transmitting a computer readable record described herein, e.g., over a computer network.

Each of the limitations of the invention can encompass various embodiments of the invention. It is, therefore anticipated that each of the limitations of the invention involving any one element or combinations of elements can be included in each aspect of the invention.

DETAILED DESCRIPTION

Figure 1A:
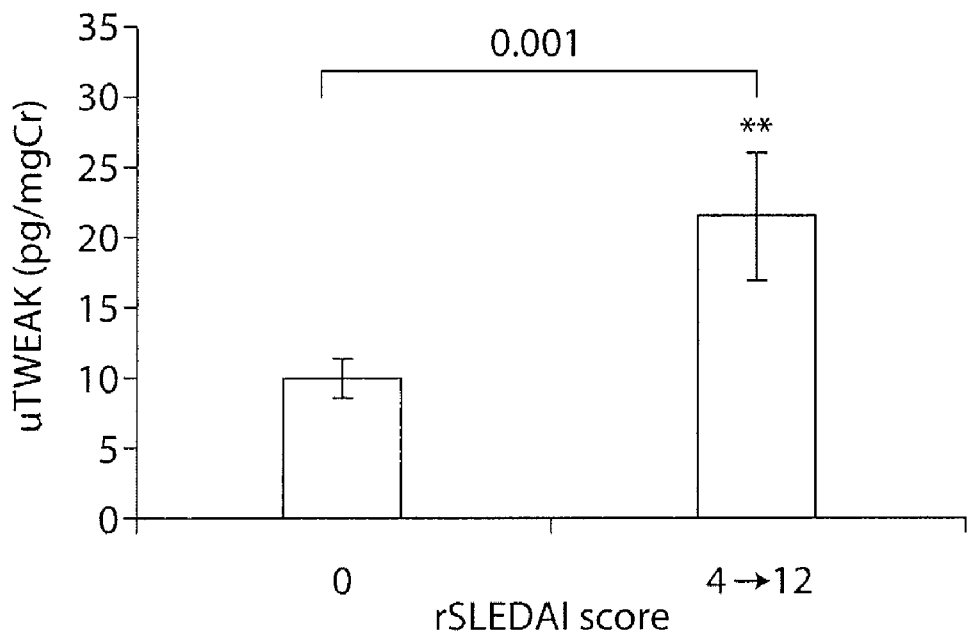
FIG. 1 shows that uTWEAK levels correlate with lupus nephritis (LN) activity. A) comparison of uTWEAK levels between 43 patients with active renal disease (defined as patients with rSLEDAI score of $\geq 4$), to 35 patients with non-active renal disease (including patients with no previous renal involvement and those with previous kidney involvement, but in which the renal disease is inactive, all with rSLEDAI score of 0). B) comparison of rSLEDAI scores of 78 SLE patients with their levels of uTWEAK yields a positive ($\rho=0.405$), significant (P<0.001) correlation.

It has been found that increased Tweak or TweakR urinary, serum, plasma or CSF levels correlate with increased severity, stage and/or activity of certain disorders. The methods described herein provide, inter alia, simple, quick, relatively non-invasive techniques for evaluating, staging, and/or diagnosing a subject for a disease, e.g., an inflammatory condition, e.g., before, during and/or after a treatment is begun. The condition can be, e.g., nephritis (e.g., lupus nephritis), RA, PsA, lupus, fibrosis, cancer, or a neurodegenerative disease (e.g., a neurodegenerative disease described herein).

Detection and Diagnosis of Nephritis

Although nephritis is discussed herein below as an exemplary disorder relating to the methods described herein, it is understood that the etiology and clinical characteristics of other conditions described herein are known to the skilled practitioner.

Nephritis is an inflammation of the kidneys. The two most common causes of nephritis are infection and auto-immune processes. Nephritis can be a symptom of underlying conditions such as systemic lupus erythematosus (SLE), diabetes, renal tuberculosis, or yellow fever. Lupus nephritis is an inflammation of the kidney caused by SLE. At least three potentially overlapping, immuno-pathogenic mechanisms are supported by experimental data. First, circulating immune complexes consisting chiefly of DNA and anti-DNA are deposited in the kidney. Resulting complement activation and chemotaxis of neutrophils leads to a local inflammatory process. Second, in situ formation of antigen and antibody complexes may similarly lead to complement activation and leukocyte mediated injury. Third, antibodies against specific cellular targets may produce renal injury. For example, antibodies, such as anti-ribosomal P, may bind to cytoplasmic antigens that have been translocated to the cell membrane with subsequent penetration and disruption of cellular function.

Glomerulonephritis is the most common type of nephritis and can include nephritic syndrome, nephrotic syndrome, and/or asymptomatic proteinuria and hematuria syndrome, all of which may lead to end stage renal disease (ESRD) and kidney failure. Lupus nephritis can involve various internal structures of the kidney and can include interstitial nephritis, glomerulonephritis (GN), mesangial GN, membranous GN, diffuse proliferative GN and/or membranoproliferative GN.

Nephritis can be detected or diagnosed by a variety of techniques, including urinalysis, e.g., detection of protein, casts, and/or red blood cells present in the urine; and/or BUN and/or creatinine tests to assess kidney function. Indications of lupus nephritis can also include high anti-DNA levels, high anti-dsDNA levels, low complement levels, high anti-nuclear antibody (ANA) panel titers and/or a positive lupus erythematosus test. Kidney X-rays or other imaging techniques and/or a kidney biopsy may also be performed. Any of these tests may be used in addition to the methods described herein.

Lupus nephritis (LN) remains a major cause of morbidity and mortality in SLE patients. Although the definition of renal involvement varies, overt renal disease is found in at least one-third to one-half of SLE patients, with reports of 5-year renal survival with treatment ranging from 46-95%. Early diagnosis and prompt treatment, however, may significantly improve long-term prognosis.

Lupus nephritis has been traditionally divided into six classes, defined by the World Health Organization (WHO) in 1982 (Churg and Sonbin. Classification and Atlas of Glomerular Disease. Tokyo: Igaku-Shoin; 1982) which take into account the renal histopathological changes together with activity of the nephritis. The prognosis and treatment of LN is heavily dependent upon this disease classification. Currently, the most accurate and reliable method to diagnose and prognosticate LN, both in terms of the activity and the chronicity of the renal processes, is by performing a biopsy. However, kidney biopsy, being an invasive procedure, can be accompanied by significant morbidity, and therefore is not usually performed serially. Furthermore, with an essentially "blind" needle biopsy there can be a question of how representative the limited number of glomeruli usually obtained are of the status of the kidney.

Evaluating a Subject for Tweak or Fn14

Techniques for evaluating a subject for Tweak or Fn14 (or other biomarker described herein) in a biological sample of the subject are known in the art. Such techniques can include detecting the presence, levels, expression or activity of a Tweak or Tweak-R protein, e.g., by qualitative or quantitative analysis of mRNA, cDNA, or protein, or by evaluating one or more nucleotides in a nucleic acid (genomic, mRNA, or cDNA) encoding Tweak or Tweak-R. Such techniques include methods for protein detection (e.g., Western blot or ELISA), and hybridization-based methods for nucleic acid detection (e.g., PCR or Northern blot). For example, an immunoassay can be used to detect Tweak protein, e.g., in a urine sample of the subject. In other embodiments, the method can include administering a labeled Tweak or Tweak-R binding agent (e.g., an antibody) to a subject, and evaluating localization of the labeled binding agent in the subject, e.g., by imaging the subject (e.g., imaging at least a portion of the kidney of the subject).

Kits: A kit can be used for assaying the Tweak pathway for risk, presence, stage or severity of a condition described herein, e.g., nephritis and/or lupus nephritis. The kit includes one or more reagents (e.g., an anti-Tweak antibody) capable of detecting one or more of: Tweak, TweakR or a biomarker described herein, in a biological sample of a subject, e.g., a human; and instructions for using the reagent to evaluate risk, predisposition, or prognosis for renal inflammation in a subject. Such a kit can include instructions to use (e.g., to contact the agent) with a sample from a subject (preferably a human) having lupus or other inflammatory disorder, or risk therefor. In a preferred embodiment, the instructions comprise instructions for use by or for a subject who has normal kidney function as defined by a clinical measure. The instructions can include directions to contact the agent with a urine sample of the subject.

The reagent can be attached to a solid substrate, e.g., a microtiter well, a tube, a sheet (e.g., a nitrocellulose sheet), a dipstick or other test device. Preferably, the kit includes a dipstick or other test device. In a preferred embodiment, the reagent is an antibody or other binding protein. The antibody can be attached to a detectable label, e.g., an enzyme, a calorimetric reagent, a fluorescent substance, or a radioactive isotope. The kit can include a positive and/or a negative control (e.g., a sample that includes an appropriate concentration of Tweak or the biomarker), e.g., with a stabilizer and/or preservative. The kit can also include a densitometer, or electrochemical strip.

Information about evaluating a subject can be obtained in a method that includes: supplying a test substrate (e.g., a tube, a strip, a dipstick, other test device, or a well) to which is attached an agent capable of detecting one or more of: Tweak or a biomarker described herein; and supplying instructions to contact the test substrate with a subject's urine. The method optionally includes supplying instructions for reading, evaluating or interpreting the contacted substrate, e.g., to evaluate risk for, predisposition, or presence of renal inflammation. The method can be performed by health care provider or a third person, or by the subject.

Other possible approaches include the use of electrochemical sensor strips, such as those used for home glucose testing, onto which a sample is placed, and which strips include reagents for initiating a reaction when wetted by the sample. The sensor strip is inserted into a meter that measures, e.g., diffusion-limited current of a reaction species indicative of the analyte of interest, e.g., Tweak and a biomarker whose expression modulated (e.g., increased) by Tweak (e.g., RANTES, KC, and/or IP-10). The meter then yields a display indicative of the concentration of analyte in the sample.

Arrays: Arrays are also particularly useful molecular tools for characterizing a sample, e.g., a sample from a subject. For example, an array having capture probes for multiple genes, including probes for Tweak and/or other biomarkers, or for multiple proteins, can be used in a method described herein. Altered expression of Tweak nucleic acids and/or protein can be used to evaluate a sample, e.g., a sample from a subject, e.g., to evaluate a disorder described herein.

Arrays can have many addresses, e.g., locatable sites, on a substrate. The featured arrays can be configured in a variety of formats, non-limiting examples of which are described below. The substrate can be opaque, translucent, or transparent. The addresses can be distributed, on the substrate in one dimension, e.g., a linear array; in two dimensions, e.g., a planar array; or in three dimensions, e.g., a three dimensional array. The solid substrate may be of any convenient shape or form, e.g., square, rectangular, ovoid, or circular.

Arrays can be fabricated by a variety of methods, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin based methods (e.g., as described in U.S. Pat. No. 5,288,514), and bead based techniques (e.g., as described in PCT US/93/04145).

The capture probe can be a single-stranded nucleic acid, a double-stranded nucleic acid (e.g., which is denatured prior to or during hybridization), or a nucleic acid having a single-stranded region and a double-stranded region. Preferably, the capture probe is single-stranded. The capture probe can be selected by a variety of criteria, and preferably is designed by a computer program with optimization parameters. The capture probe can be selected to hybridize to a sequence rich (e.g., non-homopolymeric) region of the gene. The Tm of the capture probe can be optimized by prudent selection of the complementarity region and length. Ideally, the Tm of all capture probes on the array is similar, e.g., within 20, 10, 5, 3, or 2° C. of one another.

The isolated nucleic acid is preferably mRNA that can be isolated by routine methods, e.g., including DNase treatment to remove genomic DNA and hybridization to an oligo-dT coupled solid substrate (e.g., as described in Current Protocols in Molecular Biology, John Wiley & Sons, N.Y). The substrate is washed, and the mRNA is eluted.

The isolated mRNA can be reversed transcribed and optionally amplified, e.g., by rtPCR, e.g., as described in (U.S. Pat. No. 4,683,202). The nucleic acid can be an amplification product, e.g., from PCR (U.S. Pat. Nos. 4,683,196 and 4,683,202); rolling circle amplification ("RCA," U.S. Pat. No. 5,714,320), isothermal RNA amplification or NASBA (U.S. Pat. Nos. 5,130,238; 5,409,818; and 5,554,517), and strand displacement amplification (U.S. Pat. No. 5,455,166). The nucleic acid can be labeled during amplification, e.g., by the incorporation of a labeled nucleotide. Examples of preferred labels include fluorescent labels, e.g., red-fluorescent dye Cy5 (Amersham) or green-fluorescent dye Cy3 (Amersham), and chemiluminescent labels, e.g., as described in U.S. Pat. No. 4,277,437. Alternatively, the nucleic acid can be labeled with biotin, and detected after hybridization with labeled streptavidin, e.g., streptavidin-phycoerythrin (Molecular Probes).

The labeled nucleic acid can be contacted to the array. In addition, a control nucleic acid or a reference nucleic acid can be contacted to the same array. The control nucleic acid or reference nucleic acid can be labeled with a label other than the sample nucleic acid, e.g., one with a different emission maximum. Labeled nucleic acids can be contacted to an array under hybridization conditions. The array can be washed, and then imaged to detect fluorescence at each address of the array.

The expression level of a Tweak or other biomarker can be determined using an antibody specific for the polypeptide (e.g., using a western blot or an ELISA assay). Moreover, the expression levels of multiple proteins, including Tweak and the exemplary biomarkers provided herein, can be rapidly determined in parallel using a polypeptide array having antibody capture probes for each of the polypeptides. Antibodies specific for a polypeptide can be generated by a method described herein (see "Antibody Generation"). The expression level of a TWEAK and the exemplary biomarkers provided herein can be measured in a subject (e.g., in vivo imaging) or in a biological sample from a subject (e.g., blood, serum, plasma, or synovial fluid).

A low-density (96 well format) protein array has been developed in which proteins are spotted onto a nitrocellulose membrane (Ge (2000) Nucleic Acids Res. 28, e3, I-VII). A high-density protein array (100,000 samples within 222×222 mm) used for antibody screening was formed by spotting proteins onto polyvinylidene difluoride (PVDF) (Lueking et al. (1999) Anal. Biochem. 270:103-111). See also, e.g., Mendoza et al. (1999). Biotechniques 27:778-788; MacBeath and Schreiber (2000) Science 289:1760-1763; and De Wildt et al. (2000). Nature Biotech. 18:989-994. These art-known methods and other can be used to generate an array of antibodies for detecting the abundance of polypeptides in a sample. The sample can be labeled, e.g., biotinylated, for subsequent detection with streptavidin coupled to a fluorescent label. The array can then be scanned to measure binding at each address.

The nucleic acid and polypeptide arrays of the invention can be used in wide variety of applications. For example, the arrays can be used to analyze a patient sample. The sample is compared to data obtained previously, e.g., known clinical specimens or other patient samples. Further, the arrays can be used to characterize a cell culture sample, e.g., to determine a cellular state after varying a parameter, e.g., exposing the cell culture to an antigen, a transgene, or a test compound.

The expression data can be stored in a database, e.g., a relational database such as a SQL database (e.g., Oracle or Sybase database environments). The database can have multiple tables. For example, raw expression data can be stored in one table, wherein each column corresponds to a gene being assayed, e.g., an address or an array, and each row corresponds to a sample. A separate table can store identifiers and sample information, e.g., the batch number of the array used, date, and other quality control information.

Expression profiles obtained from gene expression analysis on an array can be used to compare samples and/or cells in a variety of states as described in Golub et al. ((1999) Science 286:531). In one embodiment, expression (e.g., mRNA expression or protein expression) information for a gene encoding TWEAK and/or a gene encoding a exemplary biomarker provided herein are evaluated, e.g., by comparison a reference value, e.g., a reference value. Reference values can be obtained from a control, a reference subject. Reference values can also be obtained from statistical analysis, e.g., to provide a reference value for a cohort of subject, e.g., age and gender matched subject, e.g., normal subjects or subject who have rheumatoid arthritis or other disorder described herein. Statistical similarity to a particular reference (e.g., to a reference for a risk-associated cohort) or a normal cohort can be used to provide an assessment (e.g., an indication of risk of inflammatory disorder) to a subject, e.g., a subject who has not been diagnosed with a disorder described herein.

Subjects suitable for treatment can also be evaluated for expression and/or activity of TWEAK and/or other biomarker. Subjects can be identified as suitable for treatment (e.g., with a TWEAK blocking agent), if the expression and/or activity for TWEAK and/or the other biomarker is elevated relative to a reference, e.g., reference value, e.g., a reference value associated with normal.

Subjects who are being administered an agent described herein or other treatment can be evaluated as described for expression and/or activity of TWEAK and/or other biomarkers described herein. The subject can be evaluated at multiple times. e.g., at multiple times during a course of therapy, e.g., during a therapeutic regimen. Treatment of the subject can be modified depending on how the subject is responding to the therapy. For example, a reduction in TWEAK expression or activity or a reduction in the expression or activity of genes stimulated by TWEAK can be indicative of responsiveness.

Particular effects mediated by an agent may show a difference (e.g., relative to an untreated subject, control subject, or other reference) that is statistically significant (e.g., P value <0.05 or 0.02). Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02.

Any combination of the above methods can also be used. The above methods can be used to evaluate any genetic locus, e.g., in a method for analyzing genetic information from particular groups of individuals or in a method for analyzing a polymorphism associated with a disorder described herein, e.g., rheumatoid arthritis, e.g., in a gene encoding TWEAK or another biomarker described herein.

Tweak-Tweak Receptor Blocking Agents

Tweak pathway inhibitors to treat nephritis include Tweak/Tweak-R blocking agents. The agent may be any type of compound (e.g., small organic or inorganic molecule, nucleic acid, protein, or peptide mimetic) that can be administered to a subject.

In one embodiment, the blocking agent is a biologic, e.g., a protein having a molecular weight of between 5-300 kDa. For example, a Tweak/Tweak-R blocking agent may inhibit binding of Tweak to a Tweak receptor. A typical Tweak/Tweak-R blocking agent can bind to Tweak or a Tweak receptor, e.g., Fn14. A Tweak/Tweak-R blocking agent that binds to Tweak may block the binding site on Tweak or a Tweak receptor, alter the conformation of Tweak or a Tweak receptor, or otherwise decrease the affinity of Tweak for a Tweak receptor or prevent the interaction between Tweak and a Tweak receptor. A Tweak/Tweak-R blocking agent (e.g., an antibody) may bind to Tweak or to a Tweak receptor with a Kd of less than 10-6, 10-7, 10-8, 10-9, or 10-10 M. In one embodiment, the blocking agent binds to Tweak with an affinity at least 5, 10, 20, 50, 100, 200, 500, or 1000 better than its affinity for TNF or another TNF superfamily member (other than Tweak). In one embodiment, the blocking agent binds to the Tweak receptor with an affinity at least 5, 10, 20, 50, 100, 200, 500, or 1000-fold better than its affinity for the TNF receptor or a receptor for another TNF superfamily member. A preferred Tweak/Tweak-R blocking agent specifically binds Tweak or Tweak-R, such as a Tweak or Tweak-R specific antibody, e.g., a monoclonal antibody.

The sequence of human Tweak (SEQ ID NO:1) is shown below.

```
  1 MAARRSQRRR GRRGEPGTAL LVPLALGLGL ALACLGLLLA
    VVSLGSRASL SAQEPAQEEL

61 VAEEDQDPSE LNPQTEESQD PAPFLNRLVR PRRSAPKGRK
    TRARRAIAAH YEVHPRPGQD

121 GAQAGVDGTV SGWEEARINS SSPLRYNRQI GEFIVTRAGL
    YYLYCQVHFD EGKAVYLKLD

181 LLVDGVLALR CLEEFSATAA SSLGPQLRLC QVSGLLALRP
    GSSLRIRTLP WAHLKAAPFL

241 TYFGLFQVH
```

Also included are proteins that include an amino acid sequence at least 90, 92, 95, 97, 98, 99% identical and completely identical to the mature processed region of SEQ ID NO:1 (e.g., an amino acid sequence at least 90, 92, 95, 97, 98, 99% identical or completely identical to amino acids X1-249 of SEQ ID NO:1, where amino acid X1 is selected from the group of residues 75-115 of SEQ ID NO:1, e.g., X1 is residue Arg 93 of SEQ ID NO:1) and proteins encoded by a nucleic acid that hybridizes under high stringency conditions to the DNA encoding SEQ ID NO:1. Preferably, a Tweak protein, in its processed mature form, is capable of providing at least one Tweak activity, e.g., ability to activate Fn14 and/or cell death in cortical neurons.

The sequence of human Tweak-R (SEQ ID NO:2) is shown below.

```
  1 MARGSLRRLL RLLVLGLWLA LLRSVAGEQA PGTAPCSRGS
    SWSADLDKCM DCASCRARPH

61 SDFCLGCAAA PPAPFRLLWP ILGGALSLTF VLGLLSGFLV
    WRRCRRREKF TTPIEETGGE

121 GCPAVALIQ
```

Soluble proteins that include an amino acid sequence at least 90, 92, 95, 97, 98, 99% identical to the extracellular domain of Fn14 (and Tweak-binding fragments thereof) and proteins encoded by a nucleic acid that hybridizes under high stringency conditions to a human Fn14 protein are useful in the methods described herein. Preferably, a Fn14 protein useful in the methods described herein is a soluble Fn14 (lacking a transmembrane domain) that includes a region that binds to a Tweak protein, e.g., an amino acid sequence at least 90, 92, 95, 97, 98, or 99% identical, or completely identical, to amino acids 28-X1 of SEQ ID NO:2, where amino acid X1 is selected from the group of residues 68 to 80 of SEQ ID NO:2.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

As used herein, the term "hybridizes under high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. High stringency hybridization conditions include hybridization in 6×SSC at about 45° C., followed by one or more washes in 0.2×SSC, 0.1% SDS at 65° C., or substantially similar conditions.

Exemplary Tweak/Tweak-R blocking agents include antibodies that bind to Tweak or Tweak-R and soluble forms of the Tweak-R that compete with cell surface Tweak-R for binding to Tweak. An example of a soluble form of the Tweak-R is an Fc fusion protein that includes at least a portion of the extracellular domain of Tweak-R (e.g., a soluble Tweak-binding fragment of Tweak-R), referred to as Tweak-R-Fc. Other soluble forms of Tweak-R, e.g., forms that do not include an Fc domain, can also be used. Antibody blocking agents are further discussed below. Other types of blocking agents, e.g., small molecules, nucleic acid or nucleic acid-based aptamers, and peptides, can be isolated by screening, e.g., as described in Jhaveri et al. Nat. Biotechnol. 18:1293 and U.S. Pat. No. 5,223,409. Exemplary assays for determining if an agent binds to Tweak or Tweak-R and for determining if an agent modulates a Tweak/Tweak-R interaction are described, e.g., in US 2004-0033225.

An exemplary soluble form of the Tweak-R protein includes a region of the Tweak-R protein that binds to Tweak, e.g., about amino acids 32-75, 31-75, 31-78, or 28-79 of SEQ ID NO:2. This region can be physically associated, e.g., fused to another amino acid sequence, e.g., an Fc domain, at its N- or C-terminus. The region from Tweak-R can be spaced by a linker from the heterologous amino acid sequence. U.S. Pat. No. 6,824,773 describes an exemplary Tweak-R fusion protein.

Antibodies

Exemplary Tweak/Tweak-R blocking agents include antibodies that bind to Tweak and/or Tweak-R. In on embodiment, the antibody inhibits the interaction between Tweak and a Tweak receptor, e.g., by physically blocking the interaction, decreasing the affinity of Tweak and/or Tweak-R for its counterpart, disrupting or destabilizing Tweak complexes, sequestering Tweak or a Tweak-R, or targeting Tweak or Tweak-R for degradation. In one embodiment, the antibody can bind to Tweak or Tweak-R at one or more amino acid residues that participate in the Tweak/Tweak-R binding interface. Such amino acid residues can be identified, e.g., by alanine scanning. In another embodiment, the antibody can bind to residues that do not participate in the Tweak/Tweak-R binding. For example, the antibody can alter a conformation of Tweak or Tweak-R and thereby reduce binding affinity, or the antibody may sterically hinder Tweak/Tweak-R binding. In one embodiment, the antibody can prevent activation of a Tweak/Tweak-R mediated event or activity (e.g., NF-kappaB activation).

As used herein, the term "antibody" refers to a protein that includes at least one immunoglobulin variable region, e.g., an amino acid sequence that provides an immunoglobulin variable domain or an immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')2 fragments, Fd fragments, Fv fragments, and dAb fragments) as well as complete antibodies, e.g., intact and/or full length immunoglobulins of types IgA, IgG (e.g., IgG1, IgG2, IgG3, IgG4), IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity, or may be non-functional for one or both of these activities.

The VH and VL regions can be further subdivided into regions of hypervariability, termed "complementarity determining regions" ("CDR"), interspersed with regions that are more conserved, termed "framework regions" (FR). The extent of the FR's and CDR's has been precisely defined (see, Kabat, E. A., et al. (1991) Sequences of Proteins of Immunological Interest, Fifth Edition, US Department of Health and Human Services, NIH Publication No. 91-3242; and Chothia, C. et al. (1987) J. Mol. Biol. 196:901-917). Kabat definitions are used herein. Each VH and VL is typically composed of three CDR's and four FR's, arranged from amino-terminus to carboxyl-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two beta-sheets formed of about seven beta-strands, and a conserved disulphide bond (see, e.g., A. F. Williams and A. N. Barclay (1988) Ann. Rev Immunol. 6:381-405). An "immunoglobulin variable domain sequence" refers to an amino acid sequence that can form a structure sufficient to position CDR sequences in a conformation suitable for antigen binding. For example, the sequence may include all or part of the amino acid sequence of a naturally occurring variable domain. For example, the sequence may omit one, two or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with Tweak or a Tweak receptor.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2, and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system.

One or more regions of an antibody can be human, effectively human, or humanized. For example, one or more of the variable regions can be human or effectively human. For example, one or more of the CDRs, e.g., HC CDR1, HC CDR2, HC CDR3, LC CDR1, LC CDR2, and LC CDR3, can be human. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical, or completely identical, to a human sequence encoded by a human germline segment.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762. In some cases, humanized immunoglobulins can include a non-human amino acid at one or more framework amino acid positions.

Antibody Generation

Antibodies that bind to Tweak or a Tweak-R can be generated by a variety of means, including immunization, e.g., using an animal, or in vitro methods such as phage display. All or part of Tweak or a Tweak receptor can be used as an immunogen or as a target for selection. For example, Tweak or a fragment thereof, Tweak-R or a fragment thereof, can be used as an immunogen. In one embodiment, the immunized animal contains immunoglobulin producing cells with natural, human, or partially human immunoglobulin loci. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) Nat. Gen. 7:13-21; US 2003-0070185; U.S. Pat. No. 5,789,650; and WO 96/34096.

Non-human antibodies to Tweak or a Tweak receptor can also be produced, e.g., in a rodent. The non-human antibody can be humanized, e.g., as described in EP 239 400; U.S. Pat. Nos. 6,602,503; 5,693,761; and 6,407,213, deimmunized, or otherwise modified to make it effectively human.

EP 239 400 (Winter et al.) describes altering antibodies by substitution (within a given variable region) of their complementarity determining regions (CDRs) for one species with those from another. Typically, CDRs of a non-human (e.g., murine) antibody are substituted into the corresponding regions in a human antibody by using recombinant nucleic acid technology to produce sequences encoding the desired substituted antibody. Human constant region gene segments of the desired isotype (usually gamma I for CH and kappa for CL) can be added and the humanized heavy and light chain genes can be co-expressed in mammalian cells to produce soluble humanized antibody. Other methods for humanizing antibodies can also be used. For example, other methods can account for the three dimensional structure of the antibody, framework positions that are in three dimensional proximity to binding determinants, and immunogenic peptide sequences. See, e.g., WO 90/07861; U.S. Pat. Nos. 5,693,762; 5,693,761; 5,585,089; and 5,530,101; Tempest et al. (1991) Biotechnology 9:266-271 and U.S. Pat. No. 6,407,213. Still another method is termed "humaneering" and is described, for example, in US 2005-008625.

Fully human monoclonal antibodies that bind to Tweak or a Tweak receptor can be produced, e.g., using in vitro-primed human splenocytes, as described by Boerner et al. (1991) J. Immunol. 147:86-95. They may be prepared by repertoire cloning as described by Persson et al. (1991) Proc. Nat. Acad. Sci. USA 88:2432-2436 or by Huang and Stollar (1991) J. Immunol. Methods 141:227-236; also U.S. Pat. No. 5,798,230. Large nonimmunized human phage display libraries may also be used to isolate high affinity antibodies that can be developed as human therapeutics using standard phage technology (see, e.g., Hoogenboom et al. (1998) Immunotechnology 4:1-20; Hoogenboom et al. (2000) Immunol Today 2:371-8; and US 2003-0232333).

Antibody and Protein Production

Antibodies and other proteins described herein can be produced in prokaryotic and eukaryotic cells. In one embodiment, the antibodies (e.g., scFv's) are expressed in a yeast cell such as Pichia (see, e.g., Powers et al. (2001) J. Immunol. Methods 251:123-35), Hanseula, or Saccharomyces.

Antibodies, particularly full length antibodies, e.g., IgGs, can be produced in mammalian cells. Exemplary mammalian host cells for recombinant expression include Chinese Hamster Ovary (CHO cells) (including dhfr-CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601-621), lymphocytic cell lines, e.g., NS0 myeloma cells and SP2 cells, COS cells, K562, and a cell from a transgenic animal, e.g., a transgenic mammal. For example, the cell is a mammary epithelial cell.

In addition to the nucleic acid sequence encoding the immunoglobulin domain, the recombinant expression vectors may carry additional nucleic acid sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216; 4,634,665; and 5,179,017). Exemplary selectable marker genes include the dihydrofolate reductase (DHFR) gene (for use in dhfr-host cells with methotrexate selection/amplification) and the neo gene (for G418 selection).

In an exemplary system for recombinant expression of an antibody (e.g., a full length antibody or an antigen-binding portion thereof), a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, to transfect the host cells, to select for transformants, to culture the host cells, and to recover the antibody from the culture medium. For example, some antibodies can be isolated by affinity chromatography with a Protein A or Protein G.

Antibodies (and Fc fusions) may also include modifications, e.g., modifications that alter Fc function, e.g., to decrease or remove interaction with an Fc receptor or with Clq, or both. For example, the human IgG1 constant region can be mutated at one or more residues, e.g., one or more of residues 234 and 237, e.g., according to the numbering in U.S. Pat. No. 5,648,260. Other exemplary modifications include those described in U.S. Pat. No. 5,648,260.

For some proteins that include an Fc domain, the antibody/protein production system may be designed to synthesize antibodies or other proteins in which the Fc region is glycosylated. For example, the Fc domain of IgG molecules is glycosylated at asparagine 297 in the CH2 domain. The Fc domain can also include other eukaryotic post-translational modifications. In other cases, the protein is produced in a form that is not glycosylated.

Antibodies and other proteins can also be produced by a transgenic animal. For example, U.S. Pat. No. 5,849,992 describes a method for expressing an antibody in the mammary gland of a transgenic mammal. A transgene is constructed that includes a milk-specific promoter and nucleic acid sequences encoding the antibody of interest, e.g., an antibody described herein, and a signal sequence for secretion. The milk produced by females of such transgenic mammals includes, secreted-therein, the protein of interest, e.g., an antibody or Fc fusion protein. The protein can be purified from the milk, or for some applications, used directly.

Methods described in the context of antibodies can be adapted to other proteins, e.g., Fc fusions and soluble receptor fragments.

Nucleic Acid Antagonists

In certain implementations, nucleic acid antagonists are used to decrease expression of an endogenous gene encoding Tweak or a Tweak-R, e.g., Fn14. In one embodiment, the nucleic acid antagonist is an siRNA that targets mRNA encoding Tweak or a Tweak-R. Other types of antagonistic nucleic acids can also be used, e.g., an siRNA, a ribozyme, a triple-helix former, an aptamer, or an antisense nucleic acid.

siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. Typically, the siRNA sequences are exactly complementary to the target mRNA. dsRNAs and siRNAs in particular can be used to silence gene expression in mammalian cells (e.g., human cells). See, e.g., Clemens et al. (2000) Proc. Natl. Acad. Sci. USA 97:6499-6503; Billy et al. (2001) Proc. Natl. Sci. USA 98:14428-14433; Elbashir et al. (2001) Nature. 411:494-8; Yang et al. (2002) Proc. Natl. Acad. Sci. USA 99:9942-9947, U.S. 20030166282, 20030143204, 20040038278, and 20030224432.

Anti-sense agents can include, for example, from about 8 to about 80 nucleobases (i.e. from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA (e.g., an mRNA encoding Tweak or Tweak-R) can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., the mRNA encoding Tweak or Tweak-R. The complementary region can extend for between about 8 to about 80 nucleobases. The compounds can include one or more modified nucleobases. Modified nucleobases may include, e.g., 5-substituted pyrimidines such as 5-iodouracil, 5-iodocytosine, and C5-propynyl pyrimidines such as C5-propynylcytosine and C5-propynyluracil. Other suitable modified nucleobases include N4-(C1-C12) alkylaminocytosines and N4,N4-(C1-C12) dialkylaminocytosines. Modified nucleobases may also include 7-substituted-8-aza-7-deazapurines and 7-substituted-7-deazapurines such as, for example, 7-iodo-7-deazapurines, 7-cyano-7-deazapurines, 7-aminocarbonyl-7-deazapurines. Examples of these include 6-amino-7-iodo-7-deazapurines, 6-amino-7-cyano-7-deazapurines, 6-amino-7-aminocarbonyl-7-deazapurines, 2-amino-6-hydroxy-7-iodo-7-deazapurines, 2-amino-6-hydroxy-7-cyano-7-deazapurines, and 2-amino-6-hydroxy-7-aminocarbonyl-7-deazapurines. Furthermore, N6-(C1-C12) alkylaminopurines and N6,N6-(C1-C12) dialkylaminopurines, including N6-methylaminoadenine and N6,N6-dimethylaminoadenine, are also suitable modified nucleobases. Similarly, other 6-substituted purines including, for example, 6-thioguanine may constitute appropriate modified nucleobases. Other suitable nucleobases include 2-thiouracil, 8-bromoadenine, 8-bromoguanine, 2-fluoroadenine, and 2-fluoroguanine. Derivatives of any of the aforementioned modified nucleobases are also appropriate. Substituents of any of the preceding compounds may include C1-C30 alkyl, C2-C30 alkenyl, C2-C30 alkynyl, aryl, aralkyl, heteroaryl, halo, amino, amido, nitro, thio, sulfonyl, carboxyl, alkoxy, alkylcarbonyl, alkoxycarbonyl, and the like.

Descriptions of other types of nucleic acid agents are also available. See, e.g., U.S. Pat. Nos. 4,987,071; 5,116,742; and 5,093,246; Woolf et al. (1992) Proc Natl Acad Sci USA; Antisense RNA and DNA, D. A. Melton, Ed., Cold Spring Harbor Laboratory, Cold Spring Harbor, N.Y. (1988); 89:7305-9; Haselhoff and Gerlach (1988) Nature 334:585-59; Helene, C. (1991) Anticancer Drug Des. 6:569-84; Helene (1992) Ann. N.Y. Acad. Sci. 660:27-36; and Maher (1992) Bioassays 14:807-15.

Artificial Transcription Factors

Artificial transcription factors can also be used to regulate expression of Tweak and/or Tweak-R. The artificial transcription factor can be designed or selected from a library, e.g., for ability to bind to a sequence in an endogenous gene encoding Tweak or Tweak-R, e.g., in a regulatory region, e.g., the promoter. For example, the artificial transcription factor can be prepared by selection in vitro (e.g., using phage display, U.S. Pat. No. 6,534,261) or in vivo, or by design based on a recognition code (see, e.g., WO 00/42219 and U.S. Pat. No. 6,511,808). See, e.g., Rebar et al. (1996) Methods Enzymol 267:129; Greisman and Pabo (1997) Science 275:657; Isalan et al. (2001) Nat. Biotechnol 19:656; and Wu et al. (1995) Proc. Natl. Acad. Sci. USA 92:344 for, among other things, methods for creating libraries of varied zinc finger domains.

Optionally, an artificial transcription factor can be fused to a transcriptional regulatory domain, e.g., an activation domain to activate transcription or a repression domain to repress transcription. In particular, repression domains can be used to decrease expression of endogenous genes encoding Tweak or Tweak-R. The artificial transcription factor can itself be encoded by a heterologous nucleic acid that is delivered to a cell or the protein itself can be delivered to a cell (see, e.g., U.S. Pat. No. 6,534,261). The heterologous nucleic acid that includes a sequence encoding the artificial transcription factor can be operably linked to an inducible promoter, e.g., to enable fine control of the level of the artificial transcription factor in the cell.

Pharmaceutical Compositions

A Tweak/Tweak-R blocking agent (e.g., an antibody or soluble Tweak-R protein, e.g., Tweak-R-Fc) can be formulated as a pharmaceutical composition, e.g., for administration to a subject to treat the nephritis. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge, S. M., et al. (1977) J. Pharm. Sci. 66:1-19).

The Tweak/Tweak-R blocking agent can be formulated according to standard methods. Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X).

In one embodiment, the Tweak/Tweak-R blocking agent (e.g., an antibody or Tweak-R-Fc) can be formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the Tweak/Tweak-R blocking agent may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York, 1978.

A Tweak/Tweak-R blocking agent (e.g., an antibody or soluble Tweak-R protein) can be modified, e.g., with a moiety that improves its stabilization and/or retention in circulation, e.g., in blood, serum, or other tissues, e.g., by at least 1.5, 2, 5, 10, or 50 fold. The modified blocking agent can be evaluated to assess whether it can reach sites of damage after a stroke (e.g., by using a labeled form of the blocking agent).

For example, the Tweak/Tweak-R blocking agent (e.g., an antibody or soluble Tweak-R protein) can be associated with a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used.

For example, a Tweak or a TweakR binding antibody can be conjugated to a water-soluble polymer, e.g., a hydrophilic polyvinyl polymer, e.g. polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; and branched or unbranched polysaccharides.

When the Tweak/Tweak-R blocking agent (e.g., an antibody or soluble Tweak-R protein) is used in combination with a second agent, the two agents can be formulated separately or together. For example, the respective pharmaceutical compositions can be mixed, e.g., just prior to administration, and administered together or can be administered separately, e.g., at the same or different times.

Administration

The Tweak/Tweak-R blocking agent (e.g., an antibody or soluble Tweak-R protein) can be administered to a subject, e.g., a human subject, by a variety of methods. For many applications, the route of administration is one of: intravenous injection or infusion (IV), subcutaneous injection (SC), intraperitoneally (IP), or intramuscular injection. In some cases, administration may be directly into the CNS, e.g., intrathecal or intracerebroventricular (ICV). The blocking agent can be administered as a fixed dose, or in a mg/kg dose.

The dose can also be chosen to reduce or avoid production of antibodies against the Tweak/Tweak-R blocking agent.

The route and/or mode of administration of the blocking agent can also be tailored for the individual case, e.g., by monitoring the subject, e.g., using assessment criteria discussed herein.

Dosage regimens are adjusted to provide the desired response, e.g., a therapeutic response. For example, doses in the range of 0.1-100 mg/kg, 1 mg/kg-100 mg/kg, 0.5-20 mg/kg, 0.1-10 mg/kg or 1-10 mg/kg can be administered. A particular dose may be administered more than once, e.g., at periodic intervals over a period of time (a course of treatment). For example, the dose may be administered every 2 months, every 6 weeks, monthly, biweekly, weekly, or daily, as appropriate, over a period of time to encompass at least 2 doses, 3 doses, 5 doses, 10 doses, or more.

Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with the other agent.

Single or multiple dosages may be given. Alternatively, or in addition, the blocking agent may be administered via continuous infusion. The treatment can continue for days, weeks, months or even years.

A pharmaceutical composition may include a "therapeutically effective amount" of an agent described herein. Such effective amounts can be determined based on the effect of the administered agent, or the combinatorial effect of agents if more than one agent is used. A therapeutically effective amount of an agent may also vary according to factors such as the disease state, age, sex, and weight of the individual, and the ability of the compound to elicit a desired response in the individual. A therapeutically effective amount is also one in which any toxic or detrimental effects of the composition is outweighed by the therapeutically beneficial effects.

Devices and Kits

Pharmaceutical compositions that include the Tweak/Tweak-R blocking agent (e.g., an antibody or soluble Tweak-R) can be administered with a medical device. The device can designed with features such as portability, room temperature storage, and ease of use so that it can be used in emergency situations, e.g., by an untrained subject or by emergency personnel in the field, removed to medical facilities and other medical equipment. The device can include, e.g., one or more housings for storing pharmaceutical preparations that include Tweak/Tweak-R blocking agent, and can be configured to deliver one or more unit doses of the blocking agent.

For example, the pharmaceutical composition can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other devices, implants, delivery systems, and modules are also known.

A Tweak/Tweak-R blocking agent (e.g., an antibody or soluble Tweak-R protein) can be provided in a kit. In one embodiment, the kit includes (a) a container that contains a composition that includes a Tweak or a Tweak receptor blocking agent, and optionally (b) informational material. The informational material can be descriptive, instructional, marketing or other material that relates to the methods described herein and/or the use of the agents for therapeutic benefit. In an embodiment, the kit includes also includes a second agent for treating stroke. For example, the kit includes a first container that contains a composition that includes the Tweak/Tweak-R blocking agent, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the Tweak/Tweak-R blocking agent (e.g., an antibody or soluble Tweak-R protein), e.g., in a suitable dose, dosage form, or mode of administration (e.g., a dose, dosage form, or mode of administration described herein), to treat a subject who has had a stroke or who is at risk for stroke. The information can be provided in a variety of formats, include printed text, computer readable material, video recording, or audio recording, or a information that provides a link or address to substantive material.

In addition to the blocking agent, the composition in the kit can include other ingredients, such as a solvent or buffer, a stabilizer, or a preservative. The blocking agent can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the Tweak or a Tweak receptor blocking agent and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

Combination Therapies

The methods and compositions described herein can be used in combination with other therapies for inflammatory diseases, such as corticosteroids, NSAIDs, and dialysis.

All references, including patent documents, disclosed herein are incorporated by reference in their entirety.

EXAMPLES

Example 1

Tweak is a Biomarker for Lupus Nephritis

Methods

Patients: Patients for this study were recruited from 2 lupus centers:

1) Ohio State University College of Medicine, Columbus, Ohio, which runs the Ohio SLE Study (OSS). The OSS is a prospective longitudinal investigation of risk factors for SLE flare in recurrently active patients with renal or non-renal SLE, including patients of Caucasian (70%), African American (29%) and Asian (1%) descent; and 2) the Albert Einstein College of Medicine (AECOM) Lupus Cohort, Bronx, N.Y., which includes the Jacobi and Montefiore Medical Centers lupus clinics. Altogether, lupus clinics at Jacobi and Montefiore Medical Centers regularly follow around 350 lupus patients, of Caucasian (10%), African American (45%) and Hispanic (45%) descent. The studies at both centers have been approved by their respective IRBs.

Both lupus cohorts (OSS and AECOM) follow similar procedures. Firstly, all patients enrolled fulfill at least 4 of the 1982 revised American College of Rheumatology criteria for the diagnosis of SLE. The patients are seen regularly about once every 1-2 months, and at each visit they are clinically evaluated and receive care from a physician. Routine laboratory evaluation is usually performed at each visit, including CBC, serum chemistry, ESR, CRP, serum $C_3$, $C_4$, anti-nuclear antibodies (ANA) and anti-dsDNA titers, urinalysis, spot urine protein/creatinine ratio and/or a 24 hour urine collection. However, due to different clinical needs, a number of the patients included in the cohorts underwent only partial laboratory evaluation which did not include all of the above tests. All available laboratory values were used in the analysis.

At the time of the visit, each patient provides a freshly voided urine specimen. The fresh AECOM urine samples were frozen in small aliquots without further manipulation at −80° C. for later analysis, while the samples at OSS were first centrifuged to remove sediment before being frozen at −80° C. This difference in sample handling did not materially affect the results since results were generally consistent among the 2 centers.

Classification of SLE nephritis activity status. Kidney disease activity was assessed by the renal SLEDAI (rSLEDAI) score that consists of the 4 kidney-related items of the SLE Disease Activity Index (hematuria, pyuria, proteinuria and urinary casts) (Bombardier et al., The development and validation of the SLE Disease Activity Index (SLEDAI). Arthritis Rheum 1992 vol: 35:630-40). The presence of each one of the 4 parameters gives a score of 4 points; thus, the rSLEDAI score can range from 0 (non-active renal disease) to a maximal score of 16. The patients enrolled in the OSS were additionally classified as to the presence of active or chronic stable disease, and the severity of renal and non-renal flares, based on criteria described in detail by Rovin et al (Rovin et al., J Am Soc Nephrol 2005; 16:467-73). In brief, the patients were first divided into a renal disease group (based on a kidney biopsy that demonstrated immune complex-mediated glomerulonephritis, as well as evidence of major renal manifestations past or present attributable to SLE, such as 24 hr urine protein/creatinine ratio >1 and/or elevated serum creatinine of over 1.1 mg/dl in women and 1.3 mg/dl in men) and a non-renal disease group (normal serum creatinine, urine sediment with <5 red blood cells per high-power field and no casts). The patients were further divided within the groups as to whether they were undergoing a flare, and as to the nature of that flare (renal or non-renal). Renal flares were classified as mild, moderate or severe, based on laboratory tests such as abnormal urine sediment, an elevation of serum creatinine, or a worsening in proteinuria. Non-renal flares were recognized when the patient developed one or more symptoms or signs of non-renal SLE that required the managing physician to increase therapy. These non-renal flares were also sorted into mild, moderate or severe based on the severity and life-threatening potential of the disease manifestations present.

Urinary TWEAK measurement. Urinary TWEAK (uTWEAK) levels were determined by ELISA, as follows: microtiter plates were coated with the BEB3 murine monoclonal anti-TWEAK antibody at 2 µg/ml in bicarbonate buffer overnight. The plates were then blocked by 3% BSA/PBS for 6 hours, washed, and the urine samples diluted 1:3 in 3% BSA/PBS were added. In addition, serial dilutions of recombinant soluble human TWEAK were added to the plate to construct a standard curve. The plate was then incubated overnight at 4° C., washed, and a solution of pre-mixed biotinylated murine anti-TWEAK antibody P5G9 (Campbell et al., J Immunol 2006; 176:1889-98) and avidin-horseradish peroxidase (HRP) (0.5 µg/ml and 1:250 final, respectively) added for one hour at room temperature. The plate was washed, followed by the addition of a developer solution, and the optical density read after 10-20 minutes. uTWEAK assays were performed blindly, without knowledge of the patient's disease status or activity.

Urinary MCP-1 (uMCP-1) and urokinase plasminogen activator receptor (UPAR) measurement. The levels of MCP-1 and uPAR were measured by commercial ELISA kits, according to manufacturer's directions (BioSource International, Camarillo, Calif. and R&D Systems, Minneapolis, Minn., respectively)

Cytokine levels were normalized to urine creatinine concentrations measured in the same spot urine. uTWEAK and uMCP-1 are expressed as pg/mg creatinine (pg/mg Cr), while UPAR levels are expressed as ng/mg Cr.

Standardization. To compare the C3, C4 and anti-dsDNA laboratory measurements obtained at different centers and measured in different laboratories, values were standardized by dividing the value received from the laboratory for each patient by the mid normal range at that same laboratory. For example, if the range for serum C4 in a particular laboratory was 16 to 54 and the measured value was 10, the standardized C4 was calculated as 10 divided by (16+54)/2=10/35=0.29.

Statistical Analysis. Data is shown as mean±SEM. Testing among two groups was performed by the Mann-Whitney U test. Correlations were determined by the Spearman rank correlation coefficient ($\rho$). $P<0.05$ was considered significant. The statistics program used was GraphPad Prism version 4.03 (GraphPad Software, San Diego, Calif.).

Results

The AECOM and OSS cohorts are similar in most aspects, including the age, gender, prevalence of active renal disease, and complement levels. However, significant differences between the 2 cohorts are found in the serum creatinine and proteinuria measurements. This difference may be attributed to several possible factors. While the patients in the OSS cohort were recruited from a renal clinic, patients in the AECOM cohort were recruited from lupus clinics, Furthermore, as described above, one of the criteria for inclusion in the OSS cohort was a kidney biopsy. Therefore, chronic renal changes, such as elevated serum creatinine and/or proteinuria, may have been more frequent in the OSS than in the AECOM cohort. Nevertheless, as the mean rSLEDAI score in patients with active LN is not significantly different between the 2 groups, it appears that the OSS and AECOM cohorts are relatively comparable in terms of acute inflammatory renal changes.

Figure 1B:
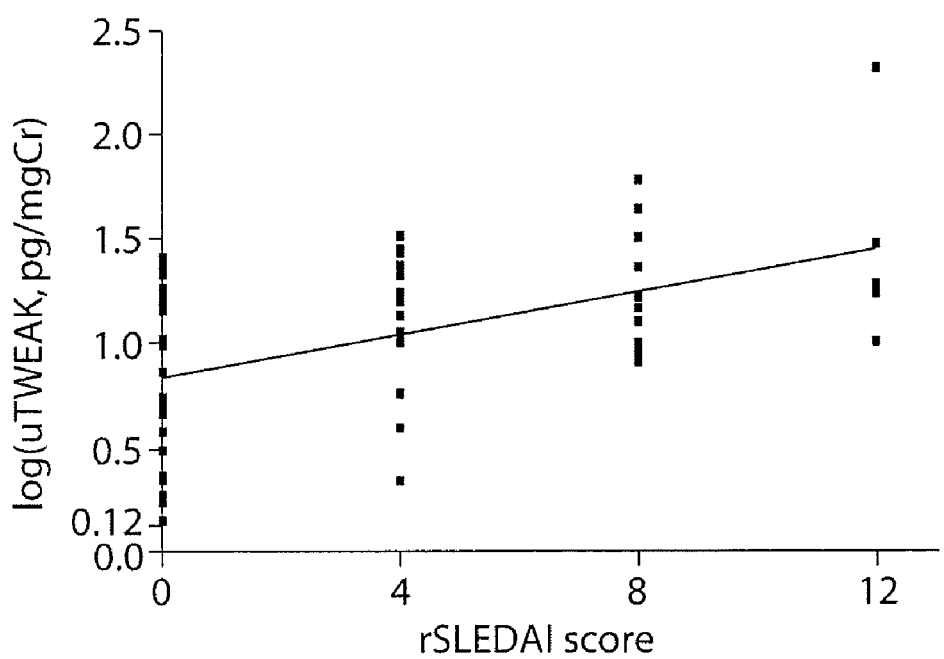
Figure 2A:
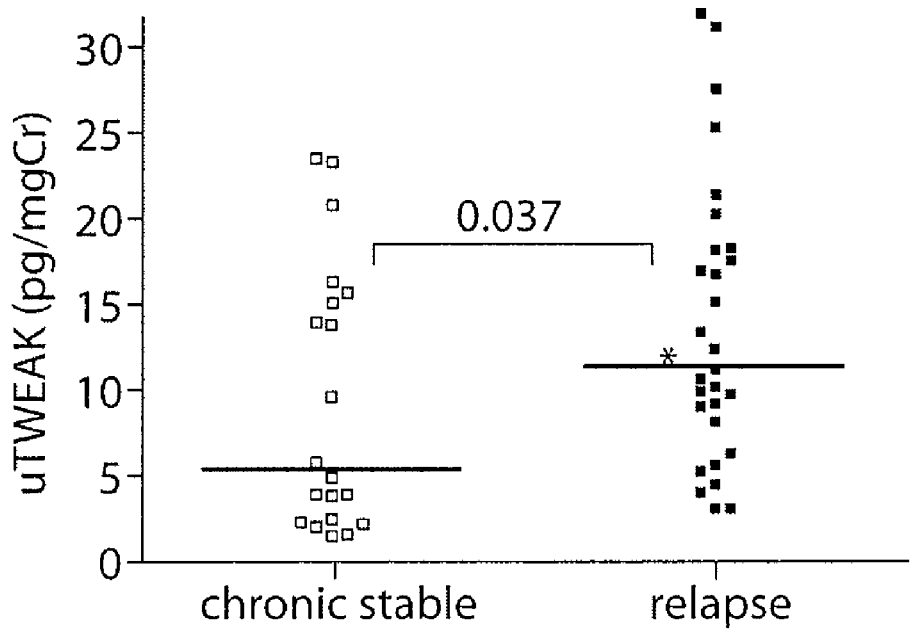
FIG. 2 shows that uTWEAK levels are higher during active disease, particularly renal flares. A) In a comparison between patients undergoing a flare and those with stable disease among all SLE patients (n=49), the flaring patients had significantly higher uTWEAK levels. Bars indicate median values. B) In patients with renal disease, both active and inactive (n=35), there was also a trend toward higher uTWEAK levels in flaring patients as opposed to chronic stable patients. Bars indicate median values.
Figure 2B:
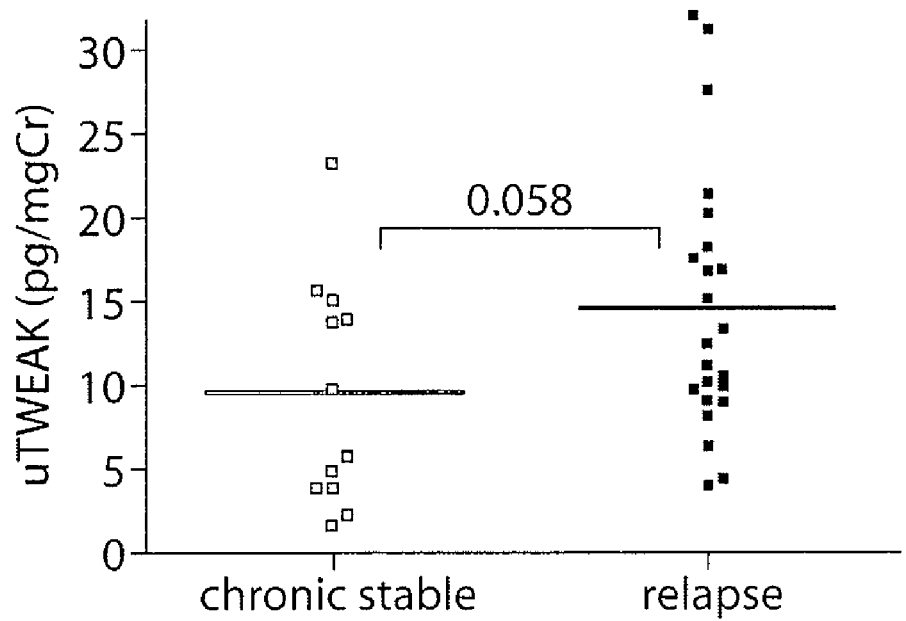
Figure 3:
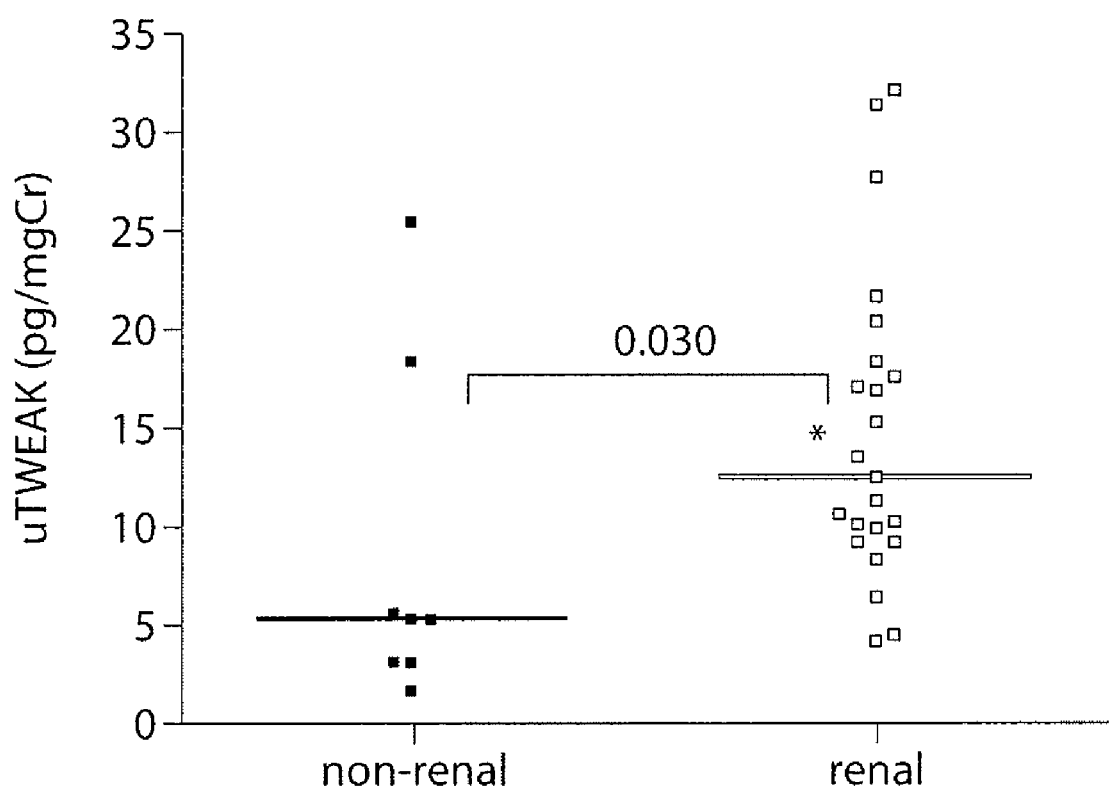
FIG. 3 shows that uTWEAK levels are significantly higher in renal than in non-renal flares. A comparison among flaring SLE patients (n=31), undergoing a renal flare or a non-renal one: patients undergoing a renal flare had significantly higher uTWEAK levels than the patients undergoing a non-renal flare. Bars indicate median values.

To determine whether TWEAK correlates with LN activity, we compared uTWEAK levels of patients with active LN (rSLEDAI score $\geq 4$) with those of patients who never had kidney involvement, or those with previous kidney involvement whose disease was quiescent, i.e. non-active renal disease (n=78). As shown in FIG. 1A, patients with active renal disease (n=43) have higher levels of uTWEAK than lupus patients with non-active or never renal disease (n=35) (21.57±4.6 versus 10.03±1.4 pg/mg Cr, P=0.001). Moreover, uTWEAK correlated significantly with rSLEDAI scores ($\rho$=0.405, P<0.001; FIG. 1B). uTWEAK levels displayed significant correlation with the total SLEDAI score, performed only in the AECOM cohort (n=30, $\rho$=0.421, P=0.022); however, this correlation was no longer significant when only non-renal components of the index were correlated with uTWEAK. When uTWEAK levels in SLE patients with chronic, stable disease (n=20) were compared with those undergoing a flare (n=31), patients with active disease had significantly higher uTWEAK levels than those with stable SLE (13.61±1.5 and 9.22±1.7 pg/mg Cr, respectively, P=0.037; FIG. 2A). Furthermore, in the more limited subgroup of lupus patients with previous renal involvement (n=35), a trend toward higher uTWEAK levels was found in patients undergoing a flare (n=23) as opposed to those with chronic stable renal disease (n=12) (14.54±1.6 and 9.39±2.0 pg/mg Cr, respectively, P=0.058; FIG. 2B). Additionally, when only patients undergoing a flare were considered separately (n=31), there were significantly higher uTWEAK levels in those patients undergoing a renal flare (n=23) as opposed to the patients undergoing a non-renal flare (n=8) (14.55±1.6 pg/mg Cr and 8.34±3.0 pg/mg Cr, respectively, P=0.03; FIG. 3). There were no significant differences between uTWEAK levels of patients with varying flare severities (mild-moderate versus severe), or with different WHO classes of LN.

Figure 4A:
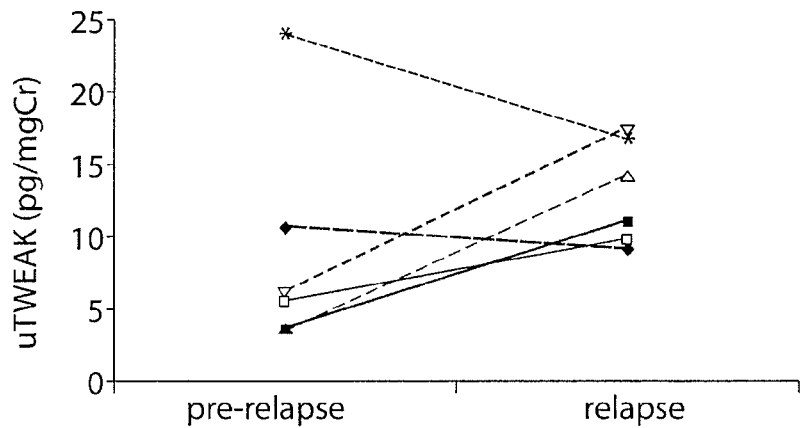
FIG. 4 shows that uTWEAK fluctuations reflect changes in renal disease activity. A) In 4 of 6 patients, uTWEAK levels increased while the patient is undergoing a renal flare. Each line represents one patient's change in uTWEAK levels between the 2 timepoints in which the samples were obtained. B) Three uTWEAK measurements in one patient over the course of a year show fluctuations in uTWEAK levels that follow the course of the patient's renal disease activity, as defined by the rSLEDAI and the presence of a disease flare. C) uTWEAK levels over 6 months match the patient's disease activity (as determined by predefined criteria), despite a stable rSLEDAI score. For B-C: The solid line shows uTWEAK levels in pg/mg Cr, and the grey bars depict rSLEDAI scores.
Figure 4B:
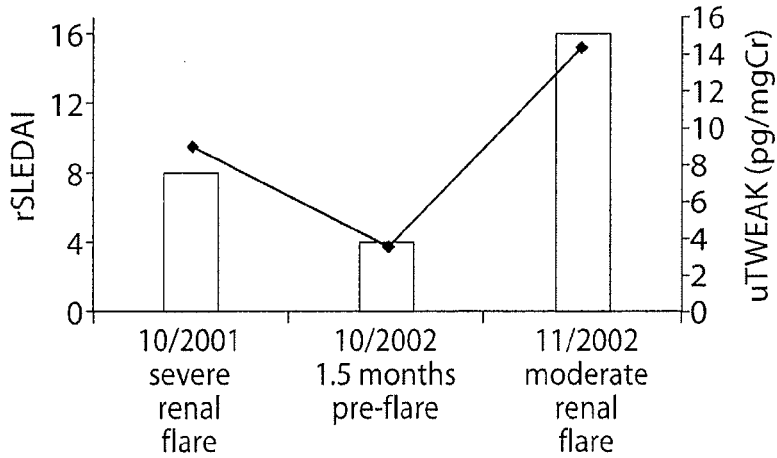
Figure 4C:
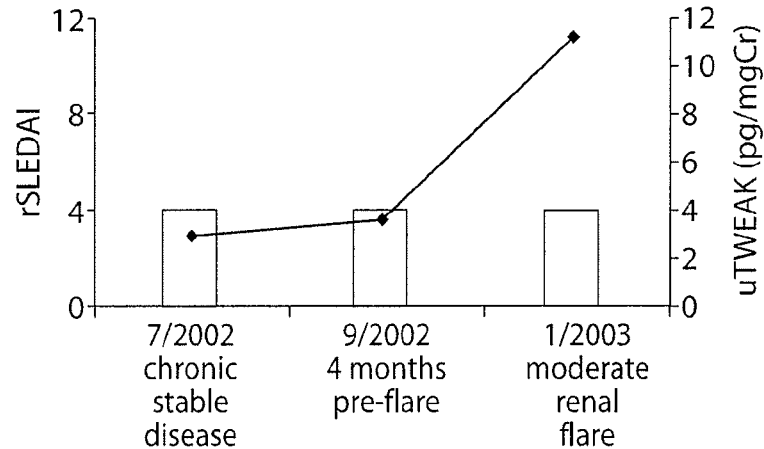

To begin to determine the utility of uTWEAK to help clinically monitor renal disease activity over time, we analyzed uTWEAK levels in the 6 patients that had 2 urine samples available, between which they transformed from a chronic stable disease state to a flare. As shown in FIG. 4A, in 4 out of the 6 patients there was a marked elevation in uTWEAK levels as the flare was developing. Among these 6 patients, 3 had uTWEAK measurements at 3 different time points. One patient had a paradoxical decrease in uTWEAK levels while undergoing a flare (dotted line in FIG. 4A). The two remaining patients are depicted in FIG. 4B-C, which demonstrate how uTWEAK levels fluctuated in parallel with renal activity (as measured by rSLEDAI) and the OSS pre-defined criteria for flare status. Furthermore, as shown in FIG. 4C, uTWEAK levels in this patient anticipated renal disease activity even better than the rSLEDAI score. While the patient's renal disease was clinically worsening and uTWEAK levels concomitantly increased, the rSLEDAI score remained unchanged.

Figure 5A:
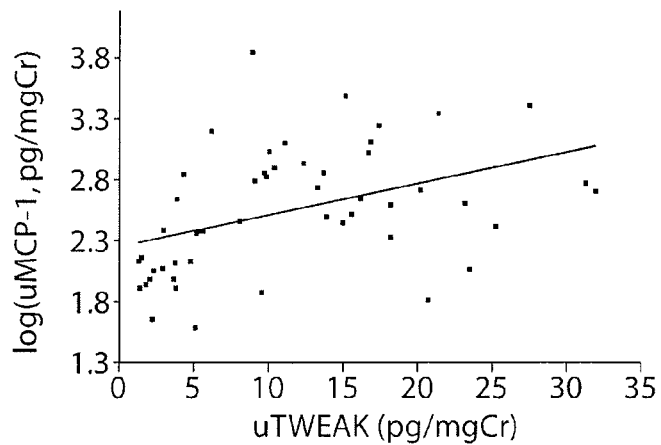
FIG. 5 shows that uTWEAK levels correlate with other biomarkers. A) uTWEAK levels significantly correlated with uMCP-1 levels, $\rho=0.501$, P<0.001, n=51. uTWEAK levels in 80 SLE patients showed negative correlation with: B) standardized serum C3 levels, $\rho=-0.262$, P=0.019, and: C) Standardized serum C4 levels, $\rho=-0.269$, P=0.016. D) uTWEAK levels correlated with standardized anti-dsDNA levels, $\rho=0.459$, P=0.008, n=32.
Figure 5B:
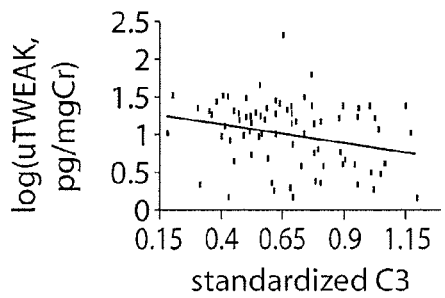
Figure 5C:
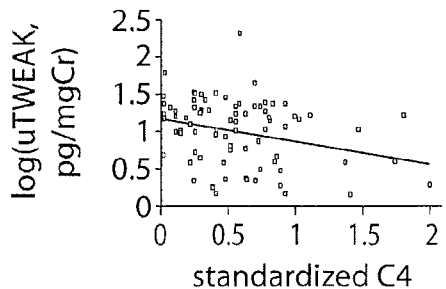
Figure 5D:
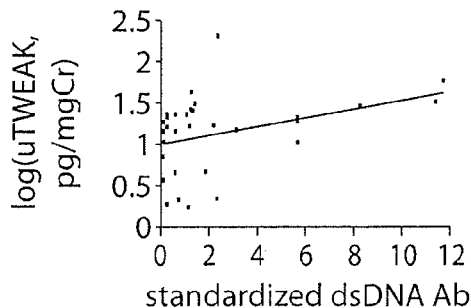

As urinary MCP-1 (uMCP-1) has already been recognized as a biomarker for LN and TWEAK stimulates the production of MCP-1 by mesangial cells and podocytes, we investigated the correlation between uMCP-1 and uTWEAK, and indeed found a strong correlation ($\rho$=0.501, P<0.001; FIG. 5A). In addition, as shown in FIG. 5B-D, uTWEAK correlated (albeit moderately) with other common serologic indicators of SLE activity such as anti-dsDNA antibodies ($\rho$=0.459, P=0.008), and complement components $C_3$ and $C_4$ ($\rho$=−0.262 and −0.269, respectively, P<0.02). Moreover, uTWEAK correlated with systemic inflammatory activity, as measured by the erythrocyte sedimentation rate ($\rho$=0.373, P=0.013) (data not shown).

We found that uTWEAK did not correlate with the degree of proteinuria (P=0.562). One likely explanation for this observation is that the source of uTWEAK is the kidneys reflecting local inflammatory activity, rather than resulting from damage to the glomerular filtration barrier and non-specific protein loss into the urine. Additional reinforcement for the above hypothesis comes from the fact that uTWEAK does not correlate with the levels of TWEAK in the serum (data not shown), indicating that uTWEAK is not simply a reflection of serum TWEAK concentrations. In addition, while urinary levels of the protein UPAR did not correlate with proteinuria ($\rho$=0.112, P=0.570; n=28), in contrast to uTWEAK, urinary UPAR levels did not correlate with renal disease activity ($\rho$=−0.024, P=0.891; n=36). This finding supports the conclusion that the correlation of uTWEAK with disease activity is specific, as not all urinary proteins correlate with renal disease activity or damage. Finally, uTWEAK negatively correlated with plasma BUN ($\rho$=−0.372, P=0.036), while a similar trend was noted with plasma creatinine ($\rho$=−0.206, P=0.066).

Example 2

Blocking Tweak Improves Glomerulonephritis

The role of TWEAK/Fn14 interactions in the pathogenesis of lupus nephritis (LN) in SLE is demonstrated.

Methods: We analyzed the effect of Fn14 deficiency on progression and severity of LN in the cGVH model of SLE. We chose this murine SLE model, as the Fn14 knockout (KO) was already bred into the C57Bl/6 (B6) background, which is susceptible to disease induction, In this model, a single injection of $10^8$ MHC II incompatible splenocytes to unirradiated mice induces autoantibodies and renal disease characteristic of lupus within 2-4 weeks. In addition, we analyzed the effect of anti-TWEAK antibodies (Ab) on Fn14 wild type (WT) mice with cGVH induced lupus.

Results: We used B6.CH2bm12/Kheg (bm12) mice, a B6 derived mouse strain with only a three amino acid change in the I-Ab chain that is sufficient to induce strong alloreactivity between B6 and bm12. We compared B6 Fn14 WT and KO mice that were each injected with bm12 donor splenocytes. Control groups not expected to develop disease included B6 WT and Fn14 KO mice injected with B6 splenocytes. We found that titers of IgG and IgM anti-dsDNA, histone, and chromatin Ab were no different between B6 Fn14 WT and KO mice injected with alloreactive splenocytes. However, kidney disease, as assessed by proteinuria, was significantly less severe in Fn14 KO mice at 6, 8, and 10 weeks. Furthermore, kidney staining for MCP-1 and RANTES was significantly decreased in Fn14 KO as compared to Fn14 WT mice with induced lupus. Finally, we found that B6 Fn14 WT mice with induced lupus treated with the P5G9 anti-TWEAK mAb (200 mg×2/week I.P.) had significantly less proteinuria than mice treated with P1.17 (isotype matched control mAb) or PBS.

CONCLUSION

Inhibition of TWEAK signaling, by genetically deleting the Fn14 receptor or by anti-TWEAK mAb treatment, significantly improved glomerulonephritis in the cGVH model of lupus. Systemic autoantibody levels were not significantly altered.

We claim:

1. A method for evaluating a test subject for status, stage, progression or severity of lupus nephritis, the method comprising:
   obtaining a biological fluid sample from the test subject; and
   determining the level of soluble Tweak (TNF-like weak inducer of apoptosis) in the sample;
   wherein the sample is a urine sample, a serum sample, or a plasma sample;
   and wherein an increase or decrease in the level of soluble Tweak as compared to a healthy subject or an earlier sample from the test subject correlates to the status, stage, progression or severity of lupus nephritis in the test subject.

2. The method of claim 1, wherein the level of soluble Tweak is determined in a urine sample from the subject.

3. The method of claim 1 or 2, wherein an increase in soluble Tweak in the sample relative to the earlier sample indicates increased activity or severity of the lupus nephritis and a decrease in soluble Tweak in the sample relative to the earlier sample indicates decreased activity or severity of the lupus nephritis.

4. The method of claim 3, wherein obtaining the sample and the earlier sample are separated by at least one week.

5. The method of claim 1 or 2, wherein the subject has or is suspected of having lupus.

6. The method of claim 1, wherein the level of soluble Tweak is determined by immunoassay.

7. The method of claim 3, wherein the determining the level of soluble Tweak in the sample comprises recording, in a print or computer readable record, the presence or level of the soluble Tweak as a diagnostic, staging or prognostic factor for the lupus nephritis.

8. The method of claim 3, wherein an increase in soluble Tweak levels is indicative of a renal flare or risk of a renal flare in the subject.

9. The method of claim 3, wherein an increase in soluble Tweak levels is indicative of increased severity or activity of the lupus nephritis.

10. The method of claim 3, wherein the evaluating steps are performed with a dipstick immunoassay.

11. A method for evaluating a test subject for status, stage, progression or severity of systemic lupus erythematosis (SLE), the method comprising:
    obtaining a biological fluid sample from the subject; and
    determining the level of soluble Tweak in the sample;
    wherein an increase or decrease in the level of soluble Tweak as compared to a healthy subject or an earlier sample from the test subject correlates to the status, stage, progression or severity of SLE in the test subject.

12. The method of claim 11, wherein the sample is selected from the group consisting of a urine sample, a serum sample, a plasma sample, a synovial fluid sample, and a cerebrospinal fluid sample.

13. The method of claim 11, wherein Tweak in the sample is evaluated in a urine sample from the subject.

14. The method of claim 11, wherein soluble Tweak in the sample is measured by immunoassay.

15. The method of claim 11, wherein the soluble Tweak in the sample is measured with a dipstick immunoassay.

16. The method of claim 11, wherein the soluble Tweak in the sample is measured with an ELISA.

17. The method of claim 11, wherein the amount of soluble Tweak in the sample is measured in a sandwich assay.

18. The method of any one of claims 1, 2, 6, or 11, wherein determining the level of soluble Tweak in the sample comprises recording, in a print or computer readable record, the presence or level of the soluble Tweak as a diagnostic, staging or prognostic factor.

* * * * *

SEQUENCE LISTING

<160> NUMBER OF SEQ ID NOS: 2

<210> SEQ ID NO 1
<211> LENGTH: 249
<212> TYPE: PRT
<213> ORGANISM: Homo sapiens

<400> SEQUENCE: 1

Met Ala Ala Arg Arg Ser Gln Arg Arg Gly Arg Gly Glu Pro
1               5                   10                  15
Gly Thr Ala Leu Leu Val Pro Leu Ala Leu Gly Leu Gly Leu Ala Leu
            20                  25                  30
Ala Cys Leu Gly Leu Leu Leu Ala Val Val Ser Leu Gly Ser Arg Ala
            35                  40                  45
Ser Leu Ser Ala Gln Glu Pro Ala Gln Glu Glu Leu Val Ala Glu Glu
        50                  55                  60
Asp Gln Asp Pro Ser Glu Leu Asn Pro Gln Thr Glu Glu Ser Gln Asp
65                  70                  75                  80
Pro Ala Pro Phe Leu Asn Arg Leu Val Arg Pro Arg Arg Ser Ala Pro
                85                  90                  95
Lys Gly Arg Lys Thr Arg Ala Arg Arg Ala Ile Ala Ala His Tyr Glu
            100                 105                 110
Val His Pro Arg Pro Gly Gln Asp Gly Ala Gln Ala Gly Val Asp Gly
            115                 120                 125
Thr Val Ser Gly Trp Glu Glu Ala Arg Ile Asn Ser Ser Ser Pro Leu
        130                 135                 140
Arg Tyr Asn Arg Gln Ile Gly Glu Phe Ile Val Thr Arg Ala Gly Leu
145                 150                 155                 160
Tyr Tyr Leu Tyr Cys Gln Val His Phe Asp Glu Gly Lys Ala Val Tyr
                165                 170                 175
Leu Lys Leu Asp Leu Leu Val Asp Gly Val Leu Ala Leu Arg Cys Leu
            180                 185                 190
Glu Glu Phe Ser Ala Thr Ala Ala Ser Ser Leu Gly Pro Gln Leu Arg
            195                 200                 205
Leu Cys Gln Val Ser Gly Leu Leu Ala Leu Arg Pro Gly Ser Ser Leu
        210                 215                 220
Arg Ile Arg Thr Leu Pro Trp Ala His Leu Lys Ala Ala Pro Phe Leu
225                 230                 235                 240
Thr Tyr Phe Gly Leu Phe Gln Val His
                245

<210> SEQ ID NO 2
<211> LENGTH: 129
<212> TYPE: PRT
<213> ORGANISM: Homo sapiens

<400> SEQUENCE: 2

Met Ala Arg Gly Ser Leu Arg Arg Leu Leu Arg Leu Leu Val Leu Gly
1               5                   10                  15
Leu Trp Leu Ala Leu Leu Arg Ser Val Ala Gly Glu Gln Ala Pro Gly
            20                  25                  30
Thr Ala Pro Cys Ser Arg Gly Ser Ser Trp Ser Ala Asp Leu Asp Lys
        35                  40                  45
Cys Met Asp Cys Ala Ser Cys Arg Ala Arg Pro His Ser Asp Phe Cys
    50                  55                  60

-continued

```
Leu Gly Cys Ala Ala Ala Pro Pro Ala Pro Phe Arg Leu Leu Trp Pro
 65                  70                  75                  80

Ile Leu Gly Gly Ala Leu Ser Leu Thr Phe Val Leu Gly Leu Leu Ser
                 85                  90                  95

Gly Phe Leu Val Trp Arg Arg Cys Arg Arg Arg Glu Lys Phe Thr Thr
             100                 105                 110

Pro Ile Glu Glu Thr Gly Gly Glu Gly Cys Pro Ala Val Ala Leu Ile
         115                 120                 125

Gln
```